(12) United States Patent
Huang et al.

(10) Patent No.: US 8,785,459 B2
(45) Date of Patent: Jul. 22, 2014

(54) QUINAZOLINE COMPOUNDS AS KINASE INHIBITORS

(75) Inventors: Jiann-Jyh Huang, New Taipei City (TW); Chu-Bin Liao, New Taipei City (TW); Pao-Nien Chen, New Taipei City (TW)

(73) Assignee: Development Center for Biotechnology, Taipei County (TW)

( * ) Notice: Subject to any disclaimer, the term of this patent is extended or adjusted under 35 U.S.C. 154(b) by 39 days.

(21) Appl. No.: 13/337,863

(22) Filed: Dec. 27, 2011

(65) Prior Publication Data

US 2013/0165458 A1    Jun. 27, 2013

(51) Int. Cl.
| | |
|---|---|
| *A01N 43/54* | (2006.01) |
| *A61K 31/517* | (2006.01) |
| *C07D 239/02* | (2006.01) |
| *C07D 401/00* | (2006.01) |
| *C07D 403/00* | (2006.01) |
| *C07D 413/00* | (2006.01) |
| *C07D 417/00* | (2006.01) |
| *C07D 419/00* | (2006.01) |

(52) U.S. Cl.
USPC .............. 514/266.23; 514/266.31; 514/266.4; 544/283; 544/284; 544/293

(58) Field of Classification Search
None
See application file for complete search history.

(56) References Cited

U.S. PATENT DOCUMENTS 6,919,338 B2 * 7/2005 Mortlock et al. .......... 514/234.5

FOREIGN PATENT DOCUMENTS

| GB | WO 9730034 | * 8/1997 | ........... C07D 239/94 |
|---|---|---|---|
| GB | 837063 | * 4/1998 | ........... C07D 403/12 |
| GB | WO 2005105761 | * 11/2005 | ........... C07D 239/94 |
| WO | WO 2005120509 | * 12/2005 | ........... A61K 31/496 |

OTHER PUBLICATIONS

Wolff et. al., "Burger's Medicinal Chemistry and Drug Discovery," 5th Ed. Part 1, pp. 975-977 (1995).*
Banker, et. al., (1996), Modern Pharmaceuticals, p. 596.*

* cited by examiner

*Primary Examiner* — Jeffrey H Murray
(74) *Attorney, Agent, or Firm* — Osha Liang LLP

(57) ABSTRACT

A compound for treating protein kinase-related disease or disorder having a structure of formula (A):

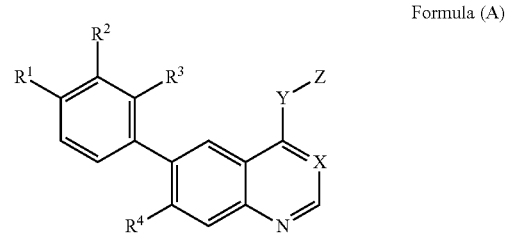

Formula (A)

wherein X is N or CH; Y is NH, O, or $CH_2$; Z is an aryl or a heteroaryl; and $R^1$, $R^2$, $R^3$, and $R^4$ are independently H, halo, nitro, cyano, aryl, heteroaryl, alkyl, alkenyl, alkynyl, cycloalkyl, heterocycloalkyl, cycloalkenyl, heterocycloalkenyl, —$OR^a$, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —$N=CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl; or $R^3$ and $R^4$ are as defined above, and $R^1$ and $R^2$ together with the carbons, to which they are attached, form a heterocycloalkenyl or heteroaryl.

3 Claims, No Drawings

QUINAZOLINE COMPOUNDS AS KINASE INHIBITORS

BACKGROUND

Protein kinases (PKs) play important roles in cellular signal pathways that regulate various cell functions such as differentiation, proliferation, migration, and apoptosis. Abnormal PK activity has been linked to and observed in a number of diseases including cancer. See K. Novak, MedGenMed. 2004; 6(2): 25. Thus, protein kinases are attractive therapeutic targets. PK inhibitors, compounds that block the activities of PKs, have been developed and used widely for clinical applications. For instance, tyrosine kinase inhibitors are useful in inhibiting T-cell proliferation and thus can be utilized as immunosuppressive agents for the prevention or treatment of graft rejection following transplant surgery and also for the prevention or treatment of autoimmune diseases (e.g., rheumatoid arthritis, psoriasis, and HIV-AIDS).

While more than thirty PK inhibitors are currently under clinical trial for cancer treatment, there is still a need for developing new PK inhibitors to treat various disorders.

SUMMARY

Embodiments of the invention are based on the unexpected discovery that certain quinazoline compounds can inhibit activities of protein kinases (e.g., B-Raf, B-Raf (V600E), C-Raf, EGFR, EGFR (T790M), VEGFR-2, FGFR1 and CDK1). These properties allow these quinazoline compounds to be applied in treating protein kinase-related diseases including cancer.

In one aspect, embodiments of the invention relate to quinazoline compounds of formula (A):

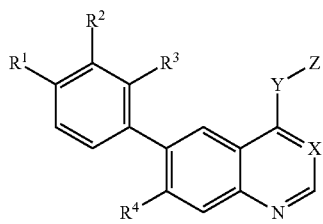

Formula (A)

wherein X is N or CH; Y is NH, O, or $CH_2$; Z is an or a heteroaryl; and $R^1$, $R^2$, $R^3$, and $R^4$ are independently H, halo, nitro, cyano, aryl, heteroaryl, alkyl, alkenyl, alkynyl, cycloalkyl, heterocycloalkyl, cycloalkenyl, heterocycloalkenyl, —$OR^a$, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —N=$CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl; or $R^3$ and $R^4$ are as defined above, and $R^1$ and $R^2$ together with the carbons, to which they are attached, form a heterocycloalkenyl or a heteroaryl, wherein the heteroaryl may be pyrrole, furan, thiophene, pyrazole, or imidazole.

Some embodiments of the invention relate to compounds of Formula (A), wherein X is CH. Some embodiments of the invention relate to compounds of Formula (A), wherein X is N.

Some embodiments of the invention relate to compounds of Formula (A), wherein X is CH and Y is NH. Some embodiments of the invention relate to compounds of Formula (A), wherein X is CH and Y is O, Some embodiments of the invention relate to compounds of Formula (A), wherein X is CH and Y is $CH_2$. Some embodiments of the invention relate to compounds of Formula (A), wherein X is N and Y is NH. Some embodiments of the invention relate to compounds of Formula (A), wherein X is N and Y is O, Some embodiments of the invention relate to compounds of Formula (A), wherein X is N and Y is $CH_2$.

Some embodiments of the invention relate to the any of above-described Formula (A) compounds, wherein $R^1$ and $R^2$ together with the carbons, to which they are attached, form a heterocycloalkenyl or a heteroaryl, wherein the heteroaryl is pyrrole, furan, thiophene, pyrazole, or imidazole.

In one aspect, the Z group in compounds of Formula (A) is an aryl group and the quinazoline compounds have a structure represented by formula (I):

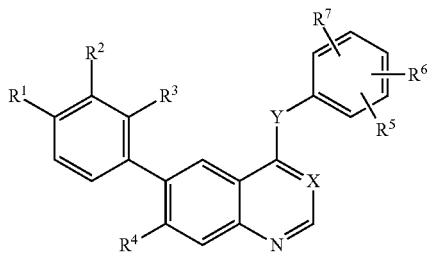

Formula (I)

wherein $R^5$, $R^6$, and $R^7$ are independently H, halo, nitro, cyano, aryl, heteroaryl, alkyl, alkenyl, alkynyl, cycloalkyl, heterocycloalkyl, cycloalkenyl, heterocycloalkenyl, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —N=$CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl; or two of $R^5$, $R^6$, and $R^7$ together with the carbons, to which they are attached, form a cycloalkenyl, heterocycloalkenyl, aryl, or heteroaryl.

Some embodiments of the invention relate to compounds of Formula (I), wherein X is CH. Some embodiments of the invention relate to compounds of Formula (I), wherein X is N.

Some embodiments of the invention relate to compounds of Formula (I), wherein X is CH and Y is NH. Some embodiments of the invention relate to compounds of Formula (I), wherein X is CH and Y is O, Some embodiments of the invention relate to compounds of Formula (I), wherein X is CH and Y is $CH_2$. Some embodiments of the invention relate to compounds of Formula (I), wherein X is N and Y is NH. Some embodiments of the invention relate to compounds of Formula (I), wherein X is N and Y is O, Some embodiments of the invention relate to compounds of Formula (I), wherein X is N and Y is $CH_2$.

Some embodiments of the invention relate to any of the above-described Formula (I) compounds, wherein $R^1$ and $R^2$ together with the carbons, to which they are attached, form a heteroaryl, wherein the heteroaryl is pyrrole, furan, thiophene, pyrazole, or imidazole.

In one aspect, the Z group in compounds of Formula (A) is a heteroaryl group and the quinazoline compounds have a structure represented by Formula (II):

Formula (II)

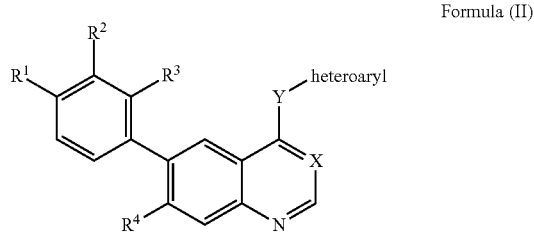

wherein X, Y, $R^1$, $R^2$, $R^3$, and $R^4$, are as defined above, and wherein the heteroaryl is selected from the following:

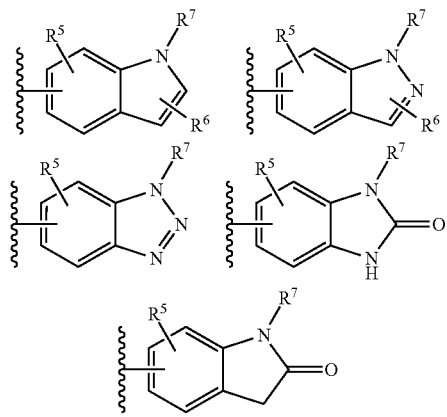

wherein each of $R^5$, $R^6$, and $R^7$ is independently H, halo, nitro, cyano, aryl, heteroaryl, cycloalkyl, heterocycloalkyl, cycloalkenyl, heterocycloalkenyl, $OR^a$, $NR^aR^b$, —$S(O)_2R^a$, —$S(O)_2NR^aR^b$, —$C(O)R^a$, —$C(O)NR^aR^b$, —$NR^aC(O)R^b$, —$NR^aS(O)_2R^b$, —$N=CR^aR^b$, or —$NR^aC(O)NHR^b$, in which each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, are heteroaryl, heterocycloalkyl, or heterocycloalkenyl.

Some embodiments of the invention relate to compounds of Formula (I), wherein X is CH. Some embodiments of the invention relate to compounds of Formula (I), wherein X is N.

Some embodiments of the invention relate to compounds of Formula (II), wherein X is CH and Y is NH. Some embodiments of the invention relate to compounds of Formula (II), wherein X is CH and Y is O, Some embodiments of the invention relate to compounds of Formula (II), wherein X is CH and Y is $CH_2$. Some embodiments of the invention relate to compounds of Formula (II), wherein X is N and Y is NH. Some embodiments of the invention relate to compounds of Formula (II), wherein X is N and Y is O, Some embodiments of the invention relate to compounds of Formula (II), wherein X is N and Y is $CH_2$.

Some embodiments of the invention relate to any of the above-described Formula (II) compounds, wherein $R^1$ and $R^2$ together with the carbons, to which they are attached, form a heteroaryl, wherein the heteroaryl is pyrrole, furan, thiophene, pyrazole, or imidazole.

In accordance with embodiments of the invention, the quinazoline compounds described herein include the compounds themselves, as well as their salts (including pharmaceutically acceptable salts), their solvates (including pharmaceutically acceptable solvates), their prodrugs, if applicable, and compositions comprising the quinazoline compounds.

In accordance with embodiments of the invention, a salt, for example, can be formed between an anion and a positively charged group (e.g., amino) on a quinazoline compound. Suitable anions include chloride, bromide, iodide, sulfate, bisulfate, sulfamate, nitrate, phosphate, diphosphate, citrate, hydrochlorate, hydrobromate, sulfonate, methanesulfonate, p-toluenesulfonate, 2-hydroxyethylsulfonate, benzoate, salicylate, stearate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a quinazoline compound. Suitable cations include sodium ion, potassium ion, magnesium ion, calcium ion, and an ammonium cation such as tetramethylammonium ion. The quinazoline compounds also include those salts containing quaternary nitrogen atoms.

In accordance with embodiments of the invention, examples of prodrugs include esters, amides, and other pharmaceutically acceptable derivatives, which, upon administration to a subject, are capable of providing active quinazoline compounds.

In accordance with embodiments of the invention, pharmaceutical compositions may contain one or more of the above-described quinazoline compounds for use in treating a protein kinase-related disease such as cancer, as well as such therapeutic uses and uses of the compounds for the manufacture of a medicament for treating the protein kinase-related disease.

In yet another aspect, embodiments of the invention relate to methods of decreasing the activity of at least one protein kinase by contacting the at least one protein kinase with one or more quinazoline compounds described above. In accordance with some embodiments of the invention, the target protein kinase is B-Raf, B-Raf (V600E), C-Raf, EGFR, EGFR (T790M), VEGFR-2, FGFR1 or CDK1 kinase.

Further, some embodiments of the invention relate to methods for treating a protein kinase-related disease by administering to a subject in need thereof an effective amount of one or more quinazoline compounds described above. A "protein kinase-related disease or disorder" can be a hyper-proliferation disorder (e.g., cancer), diabetes, a renal disease (e.g., a hyperproliferative disorder of the kidney), von Hippel-Lindau disease, fibrosis, osteoarthritis, an autoimmune diseases (e.g., psoriasis and rheumatoid arthritis), or a blood vessel proliferation disorder (e.g., atherosclerosis and restenosis). In particular, the protein kinase-related disease is cancer.

The details of one or more embodiments of the invention are set forth in the description below. Other features, objects, and advantages of the invention will be apparent from the detailed description of embodiments and also from the appending claims.

DETAILED DESCRIPTION

Embodiments of the invention relate to uses of quinazoline compounds to treat protein kinase-related diseases or disorders. The protein kinase related diseases or disorders include cancer. In accordance with embodiments of the invention, the protein kinases may include B-Raf, B-Raf (V600E), C-Raf, EGFR, EGFR (T790M), VEGFR-2, FGFR1, CDK1, etc.

The term "quinazoline compounds" as used herein include analogs of quinazoline compounds, in which the N at position 3 of the quinazoline is replaced with CH (see Formula (A), wherein X is CH). However, for clarity of description, these compounds (including the analogs) will be referred to generally as "quinazoline compounds."

The term "alkyl" refers to a straight or branched monovalent saturated hydrocarbon containing, unless otherwise stated, 1-20 carbon atoms (e.g., $C_1$-$C_{20}$, $C_1$-$C_{10}$, $C_1$-$C_6$, $C_1$-$C_4$, or $C_1$-$C_3$). Examples of alkyl include, but are not limited to, methyl, ethyl, n-propyl, i-propyl, n-butyl, i-butyl, and t-butyl. The alkyl group may be optionally substituted with one or more substitution groups described below.

The term "alkenyl" refers to a straight or branched monovalent hydrocarbon containing 2-20 carbon atoms (e.g., $C_2$-$C_{20}$, $C_2$-$C_{10}$, $C_2$-$C_6$, or $C_2$-$C_4$) and one or more double bonds. Examples of alkenyl include, but are not limited to, ethenyl, propenyl, allyl, and 1,4-butadienyl. The alkenyl group may be optionally substituted with one or more substitution groups described below.

The term "alkynyl" refers to a straight or branched monovalent hydrocarbon containing 2-20 carbon atoms (e.g., $C_2$-$C_{20}$, $C_2$-$C_{10}$, $C_2$-$C_6$, or $C_2$-$C_4$) and one or more triple bonds. Examples of alkynyl include, but are not limited to, ethynyl, 1-propynyl, 1- and 2-butynyl, and 1-methyl-2-butynyl. The alkynyl group may be optionally substituted with one or more substitution groups described below.

The term "alkoxy" refers to an —O-alkyl radical, wherein the "alkyl" portion is as defined above for the "alkyl" group. Examples of alkoxy include, but are not limited to, methoxy, ethoxy, n-propoxy, iso-propoxy, n-butoxy, iso-butoxy, sec-butoxy, and tert-butoxy.

The term "acyloxy" refers to an —O—C(O)—R radical in which R can be H, alkyl, alkenyl, alkynyl, cycloalkyl, cycloalkenyl, heterocycloalkyl, heterocycloalkenyl, aryl, or heteroaryl.

The term "amino" refers to $NH_2$. The term "alkylamino" refers to an —N(R)-alkyl radical, in which the "alkyl" portion is as defined above, and R can be H, alkyl, alkenyl, alkynyl, cycloalkyl, cycloalkenyl, heterocycloalkyl, heterocycloalkenyl, aryl, or heteroaryl.

The terms "amido" and "carbamido" refer to —NRC(O)R' and —C(O)NRR' radicals respectively, in which each of R and $R^1$, independently, can be H, alkyl, alkenyl, alkynyl, cycloalkyl, cycloalkenyl, heterocycloalkyl, heterocycloalkenyl, aryl, or heteroaryl.

The term "cycloalkyl" refers to a monovalent saturated hydrocarbon ring system having 3 to 30 carbon atoms (e.g., $C_3$-$C_{12}$, $C_3$-$C_{20}$, or $C_3$-$C_{30}$). Examples of cycloalkyl include, but are not limited to, cyclopropyl, cyclobutyl, cyclopentyl, cyclohexyl, cycloheptyl, cyclooctyl, and adamantanyl. The cycloalkyl group may be optionally substituted with one or more substitution groups described below.

The term "cycloalkenyl" refers to a monovalent non-aromatic hydrocarbon ring system having 3 to 30 carbons (e.g., $C_3$-$C_6$, $C_3$-$C_8$, $C_3$-$C_{12}$, $C_3$-$C_{15}$, $C_3$-$C_{20}$, or $C_3$-$C_{30}$) and one or more double bonds. Examples include cyclopentenyl, cyclohexenyl, and cycloheptenyl. The cycloalkenyl group may be optionally substituted with one or more substitution groups described below.

The term "heterocycloalkyl" refers to a monovalent non-aromatic 5-8 membered monocyclic, 8-12 membered bicyclic, or 11-14 membered tricyclic ring system, or a combination thereof, having one or more heteroatoms (such as O, N, S, or Se), wherein two or more rings may be fused with each other. Examples of heterocycloalkyl groups include, but are not limited to, piperazinyl, pyrrolidinyl, piperidinyl, dioxanyl, morpholinyl, and tetrahydrofuranyl. The heterocycloalkyl group may be optionally substituted with one or more substitution groups described below.

The term "heterocycloalkenyl" refers to a monovalent non-aromatic 5-8 membered monocyclic, 8-12 membered bicyclic, or 11-14 membered tricyclic ring system, or a combination thereof, having one or more heteroatoms (such as O, N, S, or Se) and one or more double bonds, wherein two or more rings may be fused with each other. The heterocycloalkenyl group may be optionally substituted with one or more substitution groups described below.

The term "aryl" refers to a monovalent aromatic ring system containing from 6 to 20 carbon atoms (e.g., $C_6$-$C_{20}$ aryl), including 6-carbon monocyclic ($C_6$ aryl), 10-carbon bicyclic ($C_{10}$ aryl), 14-carbon tricyclic ($C_{1-4}$ aryl), or a combination thereof, aromatic ring system, wherein two or more rings may be fused with each other. Examples of aryl groups include, but are not limited to, phenyl, naphthyl, and anthracenyl. The aryl group may be optionally substituted with one or more substitution groups described below.

The term "aryloxyl" refers to an —O-aryl, wherein the "aryl" portion is as defined above for the "aryl" group.

The term "arylamino" refers to an —N(R)-aryl in which the aryl portion is as defined above, and R can be H, alkyl, alkenyl, alkynyl, cycloalkyl, cycloalkenyl, heterocycloalkyl, heterocycloalkenyl, aryl, or heteroaryl.

The term "heteroaryl" refers to a monovalent aromatic ring system having 5-14 membered ring and one or more heteroatoms (such as O, N, S, or Se). A heteroaryl may include a 5-8 membered monocyclic, an 8-12 membered bicyclic, or an 11-14 membered tricyclic ring system, or a combination thereof, wherein two or more rings may be fused with each other. The number of carbon atoms contained in a "heteroaryl" ring is typically no less than the number of heteroatoms. For example, a 5-membered ring may contain 1-2 heteroatoms and 3-4 carbon atoms. Therefore, a 5-8 membered heteroaryl ring may be represented as "$C_3$-$C_7$ heteroaryl," an 8-12 membered heteroaryl ring may be represented as "$C_4$-$C_{11}$ heteroaryl," and an 11-14 membered heteroaryl ring may be represented as "$C_6$-$C_{13}$ heteroaryl," and a 5-14 membered heteroaryl ring may be represented as "$C_3$-$C_{13}$ heteroaryl." Examples of heteroaryl groups include pyridyl, furyl, imidazolyl, benzimidazolyl, pyrimidinyl, thienyl, quinolinyl, indolyl, thiazolyl, pyrrolyl, isoquinolinyl, purinyl, oxazolyl, pyrazolyl, and carbazolyl. The heteroaryl group may be optionally substituted with one or more substitution groups described below.

Alkyl, alkenyl, alkynyl, cycloalkyl, heterocycloalkyl, cycloalkenyl, heterocycloalkenyl, amino, alkylamino, arylamino, alkoxy, aryloxy, aryl, and heteroaryl mentioned above may be optionally substituted, i.e., they include both substituted and unsubstituted moieties. Possible substituents on amino, alkylamino, arylamino, alkoxy, aryloxy, cycloalkyl, heterocycloalkyl, cycloalkenyl, heterocycloalkenyl, aryl, and heteroaryl include, but are not limited to, $C_1$-$C_3$ alkyl, $C_1$-$C_6$ alkyl, $C_1$-$C_{10}$ alkyl, $C_2$-$C_4$ alkenyl, $C_2$-$C_6$ alkenyl, $C_2$-$C_{10}$ alkenyl, $C_2$-$C_4$ alkynyl, $C_2$-$C_6$ alkynyl, $C_2$-$C_{10}$ alkynyl, $C_3$-$C_6$ cycloalkyl, $C_3$-$C_{12}$ cycloalkyl, $C_3$-$C_{20}$ cycloalkyl, $C_3$-$C_6$ cycloalkenyl, $C_3$-$C_{12}$ cycloalkenyl, $C_3$-$C_{20}$ cycloalkenyl, $C_1$-$C_6$ heterocycloalkyl, $C_1$-$C_{10}$ heterocycloalkyl, $C_1$-$C_{20}$ heterocycloalkyl, $C_1$-$C_6$ heterocycloalkenyl, $C_1$-$C_{10}$ heterocycloalkenyl, $C_1$-$C_{20}$ heterocycloalkenyl, $C_1$-$C_3$ alkoxy, $C_1$-$C_6$ alkoxy, $C_1$-$C_{10}$ alkoxy, aryl, aryloxy, heteroaryl, heteroaryloxy, amino, $C_1$-$C_{10}$ alkylamino, arylamino, hydroxy, halo, oxo(O=), thioxo(S=), thio, silyl, alkylthio, arylthio, $C_1$-$C_{10}$ alkylsulfonyl, arylsulfonyl, acylamino, aminoacyl, aminothioacyl, amidino, mercapto, amido, thioureido, thiocyanato, sulfonamido, guanidine, ureido, cyano, nitro, acyl, thioacyl, acyloxy, carbamido, carbamyl (—C(O)NH$_2$), carboxyl (—COOH), and carboxylic ester, wherein each of this substituent is not further substituted. On the other hand, possible substituents on alkyl, alkenyl, or alkynyl include all of the above-recited substituents except $C_1$-$C_{10}$ alkyl, wherein each of this substituent is not further substituted. Cycloalkyl, cycloalkenyl, heterocycloalkyl, heterocycloalkenyl, aryl, and heteroaryl can also be fused with each other.

As used herein, the term "protein kinase-related disease" refers to a disease or condition that is characterized by abnormal PK activity or a disease or condition that can be treated with changes to the activity of at least one PK. Abnormal PK activity can arise as the result of elevated PK expression level, or presence of PK expression that does not happen under normal conditions. PK-related disease described herein include, but not limited to, cancer, diabetes, a hyper-proliferation disorder, hyperproliferative disorders of the kidney, renal disease, von Hippel-Lindau disease, restenosis, fibrosis, psoriasis, osteoarthritis, rheumatoid arthritis, an inflammatory disorder, immunological disorders such as autoimmune diseases (e.g., AIDS, lupus, etc.), cardiovascular disorders (e.g. atherosclerosis), and blood vessel proliferative disorders such as abnormal vasculogenesis.

The term "treating" refers to administering a quinazoline compound to a subject that has a protein kinase-related disease, or has a symptom of or a predisposition toward it, with the purpose to cure, heal, alleviate, relieve, alter, remedy, ameliorate, improve, affect or reduce the risk of the disorder, the symptoms of or the predisposition toward the disorder. For example, treating cancer refers to the treatment results in reduction or inhibition of cancer growth or cancer cell growth, regression in cancer growth (i.e. it reduces the size of a detectable cancer), or the disappearance of a cancer.

The term "an effective amount" refers to the amount of the active agent that is required to confer the intended therapeutic effect in the subject. Effective amounts may vary, as recognized by those skilled in the art, depending on route of administration, excipient usage, and the possibility of co-usage with other agents. One skilled in the art can determine an effective amount without undue experimentation because the procedures involved are routine practices. The subject in need of the treatment can be a mammal. The term "mammal" refers to human or nonhuman mammal, for example, dogs, cats, pigs, cows, sheep, goats, horses, rats, or mice.

As noted above, embodiments of the invention relate to uses of quinazoline compounds for treating protein kinase related diseases or disorders. Specifically, embodiments of the invention relate to quinazoline compounds of formula (A):

wherein X is N or CH; Y is NH, O, or CH$_2$; Z is an aryl or a heteroaryl; and
$R^1$, $R^2$, $R^3$, and $R^4$ are independently H, halo, nitro, cyano, aryl, heteroaryl, alkyl, alkenyl, alkynyl, cycloalkyl, heterocycloalkyl, cycloalkenyl, heterocycloalkenyl, —OR$^a$, —C(O)R$^a$, —C(O)NR$^a$R$^b$, —NR$^a$C(O)R$^b$, —NR$^a$R$^b$, —S(O)$_2$R$^a$, —S(O)$_2$NR$^a$R$^b$, —NR$^a$S(O)$_2$R$^b$, —N=CR$^a$R$^b$, or —NR$^a$C(O)NHR$^b$, wherein each of R$^a$ and R$^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or R$^a$ and R$^b$, together with the nitrogen atom to which they are bonded, form heteroaryl, heterocycloalkyl, or heterocycloalkenyl; or
$R^3$ and $R^4$ are as defined above, and $R^1$ and $R^2$ together with the carbons, to which they are attached, form a heterocycloalkenyl or a heteroaryl, wherein the heteroaryl may be pyrrole, furan, thiophene, pyrazole, or imidazole.

In compounds of the invention, each of the X, Y, $R^1$, $R^2$, $R^3$, and $R^4$ groups in Formula (A) shown above is independently selectable. Therefore, compounds of the invention include all possible combinations of the various groups listed above. Some of these compounds, which share one or more identical substitutions, may be group as a subgenus (subgroups).

For example, some compounds of the invention include compounds of Formula (A), wherein X is CH, while Y and $R^1$, $R^2$, $R^3$, and $R^4$ are as defined above. Likewise, some compounds of the invention may be compounds of Formula (A), wherein X is N, while Y and $R^1$, $R^2$, $R^3$, and $R^4$ are as defined above.

Similarly, some embodiments of the invention relate to compounds of Formula (A), wherein X is CH and Y is NH, while $R^1$, $R^2$, $R^3$, and $R^4$ are as defined above. Some embodiments of the invention relate to compounds of Formula (A), wherein X is CH and Y is O, while $R^1$, $R^2$, $R^3$, and $R^4$ are as defined above. Some embodiments of the invention relate to compounds of Formula (A), wherein X is CH and Y is CH$_2$, while $R^1$, $R^2$, $R^3$, and $R^4$ are as defined above. Some embodiments of the invention relate to compounds of Formula (A), wherein X is N and Y is NH, while $R^1$, $R^2$, $R^3$, and $R^4$ are as defined above. Some embodiments of the invention relate to compounds of Formula (A), wherein X is N and Y is O, while $R^1$, $R^2$, $R^3$, and $R^4$ are as defined above. Some embodiments of the invention relate to compounds of Formula (A), wherein X is N and Y is CH$_2$, while $R^1$, $R^2$, $R^3$, and $R^4$ are as defined above.

Furthermore, some embodiments of the invention relate to any of above-described Formula (A) compounds, wherein $R^1$ and $R^2$ together with the carbons, to which they are attached, form a heteroalkenyl or a heteroaryl, wherein the heteroaryl is pyrrole, furan, thiophene, pyrazole, or imidazole.

In accordance with some embodiments of the invention, the Z group in compounds of Formula (A) is an aryl group and the quinazoline compounds have a structure shown as formula (I):

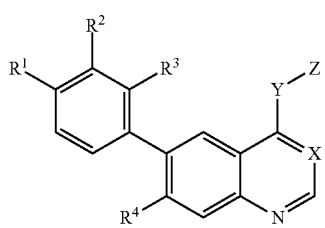

Formula (A)

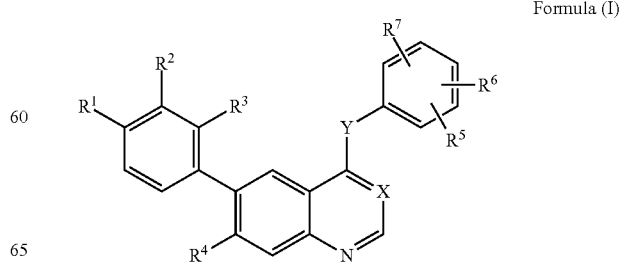

Formula (I)

wherein X, Y, R$^1$, R$^2$, R$^3$, and R$^4$ are as defined above, and
each of R$^5$, R$^6$, and R$^7$, independently, is H, halo, nitro,
cyano, aryl, heteroaryl, alkyl, alkenyl, alkynyl,
cycloalkyl, heterocycloalkyl, cycloalkenyl, heterocycloalkenyl, —OR$^a$, —C(O)R$^a$, —C(O)NR$^a$R$^b$, —NR$^a$C(O)R$^b$, —NR$^a$R$^b$, —S(O)$_2$R$^a$, —S(O)$_2$NR$^a$R$^b$, —NR$^a$S(O)$_2$R$^b$, —N=CR$^a$R$^b$, or —NR$^a$C(O)NHR$^b$, wherein
each of R$^a$ and R$^b$, independently, is H, alkyl, alkenyl,
alkynyl, aryl, aryloxy, alkoxy, hydroxy, heteroaryl,
cycloalkyl, heterocycloalkyl, cycloalkenyl, or heterocycloalkenyl, or R$^a$ and R$^b$, together with the nitrogen atom
to which they are bonded, form heteroaryl, heterocycloalkyl, or heterocycloalkenyl; or
two of R$^5$, R$^6$, and R$^7$ together with the carbons, to which
they are attached, form a cycloalkenyl, heterocycloalkenyl, aryl, or heteroaryl.

In accordance with embodiments of the invention, each of
the X, Y, R$^1$, R$^2$, R$^3$, R$^4$, R$^5$, R$^6$, and R$^7$ groups in Formula (I)
shown above is independently selectable. Therefore, compounds of the invention include all possible combinations of
the various groups listed above. Some of these compounds,
which share one or more identical substitutions, may be group
as a subgenus (subgroups).

For example, some compounds of the invention include
compounds of Formula (I), wherein X is CH, while Y and R$^1$,
R$^2$, R$^3$, and R$^4$ are as defined above. Likewise, some compounds of the invention may be compounds of Formula (I),
wherein X is N, while Y and R$^1$, R$^2$, R$^3$, and R$^4$ are as defined
above.

Similarly, some embodiments of the invention relate to
compounds of Formula (I), wherein X is CH and Y is NH,
while R$^1$, R$^2$, R$^3$, and R$^4$ are as defined above. Some embodiments of the invention relate to compounds of Formula (I),
wherein X is CH and Y is O, while R$^1$, R$^2$, R$^3$, and R$^4$ are as
defined above. Some embodiments of the invention relate to
compounds of Formula (I), wherein X is CH and Y is CH$_2$,
while R$^1$, R$^2$, R$^3$, and R$^4$ are as defined above. Some embodiments of the invention relate to compounds of Formula (I),
wherein X is N and Y is NH, while R$^1$, R$^2$, R$^3$, and R$^4$ are as
defined above. Some embodiments of the invention relate to
compounds of Formula (I), wherein X is N and Y is O, while
R$^1$, R$^2$, R$^3$, and R$^4$ are as defined above. Some embodiments
of the invention relate to compounds of Formula (I), wherein
X is N and Y is CH$_2$, while R$^1$, R$^2$, R$^3$, and R$^4$ are as defined
above.

Furthermore, some embodiments of the invention relate to
any of above-described Formula (I) compounds, wherein R$^1$
and R$^2$ together with the carbons, to which they are attached,
form a heteroaryl, wherein the heteroaryl is pyrrole, furan,
thiophene, pyrazole, or imidazole.

In accordance with some embodiments of the invention,
the Z group in compounds of Formula (A) is a heteroaryl
group and the quinazoline compounds have a structure shown
as Formula (II):

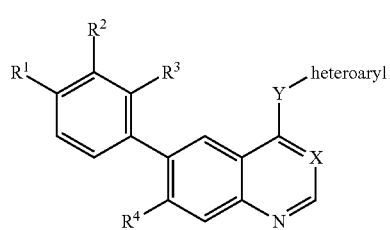

Formula (II)

wherein X, Y, R$^1$, R$^2$, R$^3$, and R$^4$ are as defined above, and a
heteroaryl group is attached to Y.

In accordance with some embodiments of the invention,
the heteroaryl group in the quinazoline compounds having a
structure of Formula (II) may be selected from the following:

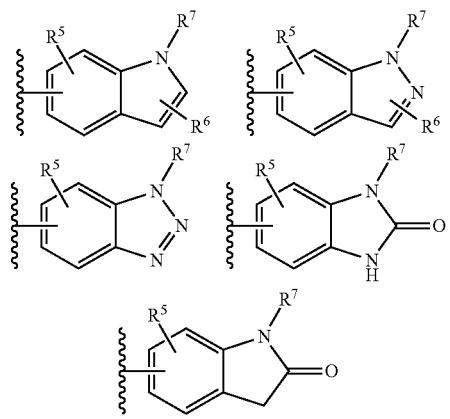

wherein R$^5$, R$^6$, and R$^7$ are as defined above.

In accordance with embodiments of the invention, each of
the X, Y, R$^1$, R$^2$, R$^3$, R$^4$, R$^5$, R$^6$, and R$^7$ groups in Formula (II)
shown above is independently selectable. Therefore, compounds of the invention include all possible combinations of
the various groups listed above. Some of these compounds,
which share one or more identical substitutions, may be group
as a subgenus (subgroups).

For example, some compounds of the invention include
compounds of Formula (II), wherein X is CH, while Y and R$^1$,
R$^2$, R$^3$, and R$^4$ are as defined above. Likewise, some compounds of the invention may be compounds of Formula (II),
wherein X is N, while Y and R$^1$, R$^2$, R$^3$, and R$^4$ are as defined
above.

Similarly, some embodiments of the invention relate to
compounds of Formula (I), wherein X is CH and Y is NH,
while R$^1$, R$^2$, R$^3$, and R$^4$ are as defined above. Some embodiments of the invention relate to compounds of Formula (II),
wherein X is CH and Y is O, while R$^1$, R$^2$, R$^3$, and R$^4$ are as
defined above. Some embodiments of the invention relate to
compounds of Formula (II), wherein X is CH and Y is CH$_2$,
while R$^1$, R$^2$, R$^3$, and R$^4$ are as defined above. Some embodiments of the invention relate to compounds of Formula (II),
wherein X is N and Y is NH, while R$^1$, R$^2$, R$^3$, and R$^4$ are as
defined above. Some embodiments of the invention relate to
compounds of Formula (II), wherein X is N and Y is O, while
R$^1$, R$^2$, R$^3$, and R$^4$ are as defined above. Some embodiments
of the invention relate to compounds of Formula (II), wherein
X is N and Y is CH$_2$, while R$^1$, R$^2$, R$^3$, and R$^4$ are as defined
above.

Furthermore, some embodiments of the invention relate to
any of above-described Formula (II) compounds, wherein R$^1$
and R$^2$ together with the carbons, to which they are attached,
form a heteroaryl, wherein the heteroaryl is pyrrole, furan,
thiophene, pyrazole, or imidazole.

In accordance with embodiments of the invention, the
quinazoline compounds described herein include the compounds themselves, as well as their salts (including pharmaceutically acceptable salts), their solvates (including pharmaceutically acceptable solvates), their prodrugs, if applicable,
and compositions comprising the quinazoline compounds.

In accordance with embodiments of the invention, a salt,
for example, can be formed between an anion and a positively
charged group (e.g., amino) on a quinazoline compound.

Suitable anions include chloride, bromide, iodide, sulfate, bisulfate, sulfamate, nitrate, phosphate, diphosphate, citrate, hydrochlorate, hydrobromate, sulfonate, methanesulfonate, p-toluenesulfonate, 2-hydroxyethylsulfonate, benzoate, salicylate, stearate, trifluoroacetate, glutamate, glucuronate, glutarate, malate, maleate, succinate, fumarate, tartrate, tosylate, salicylate, lactate, naphthalenesulfonate, and acetate. Likewise, a salt can also be formed between a cation and a negatively charged group (e.g., carboxylate) on a quinazoline compound. Suitable cations include sodium ion, potassium ion, magnesium ion, calcium ion, and an ammonium cation such as tetramethylammonium ion. The quinazoline compounds also include those salts containing quaternary nitrogen atoms.

In accordance with embodiments of the invention, examples of prodrugs include esters, amides, and other pharmaceutically acceptable derivatives, which, upon administration to a subject, are capable of providing active quinazoline compounds.

In accordance with embodiments of the invention, pharmaceutical compositions may contain one or more of the above-described quinazoline compounds for use in treating a protein kinase-related disease such as cancer. Some embodiments of the invention relate to uses of such therapeutic compositions and use of the quanazoline compounds for the manufacture of a medicament for treating the protein kinase-related diseases.

In yet another aspect, embodiments of the invention relate to methods of decreasing the activity of at least one protein kinase by contacting the at least one protein kinase with one or more quinazoline compounds described above. The target protein kinase may be B-Raf, B-Raf(V600E), C-Raf, EGFR, EGFR (T790M), VEGFR-2, FGFR1 or CDK1 kinase.

Further, some embodiments of the invention relate to methods for treating a protein kinase-related disease by administering to a subject in need thereof an effective amount of one or more quinazoline compounds described above. The protein kinase-related disease can be a hyper-proliferation disorder (e.g., cancer), diabetes, a renal disease (e.g., a hyper-proliferative disorder of the kidney), von Hippel-Lindau disease, fibrosis, osteoarthritis, an autoimmune diseases (e.g., psoriasis and rheumatoid arthritis), or a blood vessel proliferative disorder (e.g., atherosclerosis and restenosis). In particular, the protein kinase-related disease is cancer.

The quinazoline compounds in accordance with embodiments of the invention may be prepared using convention reactions as illustrated in Reaction Scheme I below. Using these procedures, compounds of Formula (A) are synthesized. Some exemplary compounds are shown in Table 1 and results of their characterization are shown in Table 2. Representative compounds of the invention are tested for their abilities to inhibit a variety of protein kinases (e.g., B-Raf, B-Raf(V600E), C-Raf, EGFR, EGFR (T790M), VEGFR-2, FGFR1, FLT3, and CDK1). Results from these tests are shown in Table 3 and Table 4. The antiproliferative activities of representative compounds are tested with several cancer cell lines and the results are shown in Table 5. Furthermore, the abilities of these compounds to inhibit tumor growth in vivo are tested in mice and the results are shown in Table 6.

Table 1 shows exemplary compounds of the invention:

TABLE 1

| Compd ID | Structure |
|---|---|
| 1 | 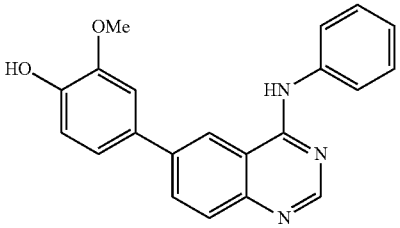 [SMILES: COc1cc(-c2ccc3ncnc(Nc4ccccc4)c3c2)ccc1O]<br>2-methoxy-4-(4-(phenylamino)quinazolin-6-yl)phenol |
| 2 | 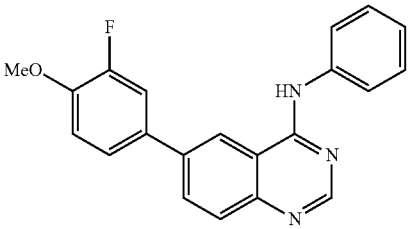 [SMILES: COc1ccc(-c2ccc3ncnc(Nc4ccccc4)c3c2)cc1F]<br>6-(3-fluoro-4-methoxyphenyl)-N-phenylquinazolin-4-amine |
| 3 | 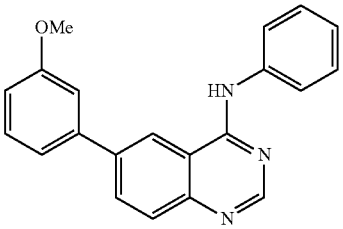 [SMILES: COc1cccc(-c2ccc3ncnc(Nc4ccccc4)c3c2)c1]<br>6-(3-methoxyphenyl)-N-phenylquinazolin-4-amine |

TABLE 1-continued
| Compd ID | Structure |
|---|---|
| 4 | 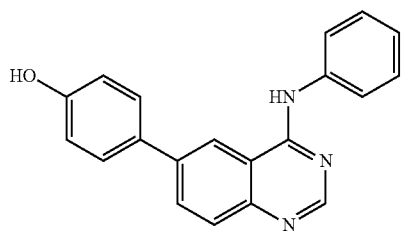 [SMILES: Oc1ccc(-c2ccc3ncnc(Nc4ccccc4)c3c2)cc1]<br>4-(4-(phenylamino)quinazolin-6-yl)phenol |
| 5 | 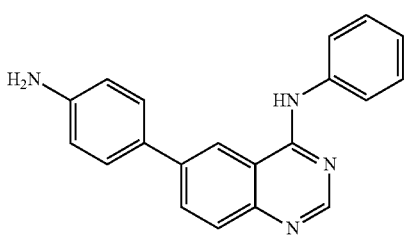 [SMILES: Nc1ccc(-c2ccc3ncnc(Nc4ccccc4)c3c2)cc1]<br>6-(4-aminophenyl)-N-phenylquinazolin-4-amine |
| 6 | 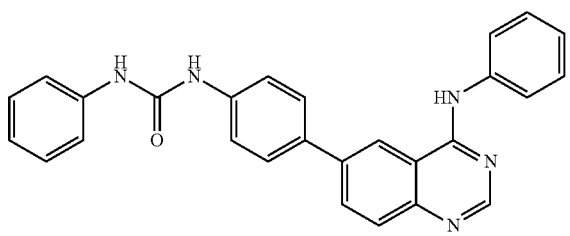 [SMILES: O=C(Nc1ccccc1)Nc1ccc(-c2ccc3ncnc(Nc4ccccc4)c3c2)cc1]<br>1-phenyl-3-(4-(4-(phenylamino)quinazolin-6-yl)phenyl)urea |
| 7 | 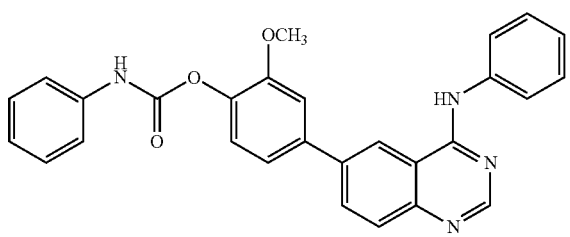 [SMILES: COc1cc(-c2ccc3ncnc(Nc4ccccc4)c3c2)ccc1OC(=O)Nc1ccccc1]<br>2-methoxy-4-(4-(phenylamino)quinazolin-6-yl)phenyl phenylcarbamate |
| 8 | 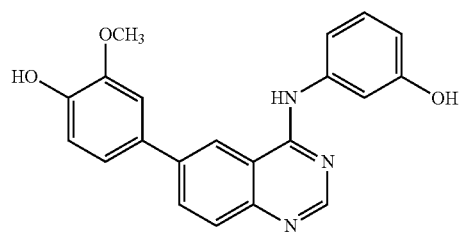 [SMILES: COc1cc(-c2ccc3ncnc(Nc4cccc(O)c4)c3c2)ccc1O]<br>4-(4-(3-hydroxyphenylamino)quinazolin-6-yl)-2-methoxyphenol |

TABLE 1-continued

| Compd ID | Structure |
| --- | --- |
| 9 | 2-methoxy-4-(4-(phenylamino)quinazolin-6-yl)phenyl ethylcarbamate |
| 10 | 6-(4-methoxyphenyl)-N-phenylquinazolin-4-amine |
| 11 | 1-(4-(4-(phenylamino)quinazolin-6-yl)phenyl)urea |
| 12 | 1-ethyl-3-(4-(4-(phenylamino)quinazolin-6-yl)phenyl)urea |
| 13 | 4-(4-(3,4-dimethoxyphenylamino)quinazolin-6-yl)-2-methoxyphenol |

TABLE 1-continued

| Compd ID | Structure |
|---|---|
| 14 | 4-(4-(3-chloro-4-fluorophenylamino)quinazolin-6-yl)-2-methoxyphenol |
| 15 | 4-(4-(4-fluorophenylamino)quinazolin-6-yl)-2-methoxyphenol |
| 16 | 4-(4-(4-chloro-2-fluorophenylamino)quinazolin-6-yl)-2-methoxyphenol |
| 17 | 4-(4-(2-fluoro-4-methylphenylamino)quinazolin-6-yl)-2-methoxyphenol |
| 18 | 2-methoxy-4-(4-(3-(trifluoromethyl)phenylamino)quinazolin-6-yl)phenol |

TABLE 1-continued

| Compd ID | Structure |
|---|---|
| 19 | 4-(4-(4-hydroxyphenylamino)quinazolin-6-yl)-2-methoxyphenol |
| 20 | 4-(4-(2,4-difluorophenylamino)quinazolin-6-yl)-2-methoxyphenol |
| 21 | 4-(4-(4-chloro-2-hydroxyphenylamino)quinazolin-6-yl)-2-methoxyphenol |
| 22 | 2-methoxy-4-(4-(3-methoxyphenylamino)quinazolin-6-yl)phenol |
| 23 | 4-(4-(2-hydroxyphenylamino)quinazolin-6-yl)-2-methoxyphenol |

TABLE 1-continued

| Compd ID | Structure |
|---|---|
| 24 | 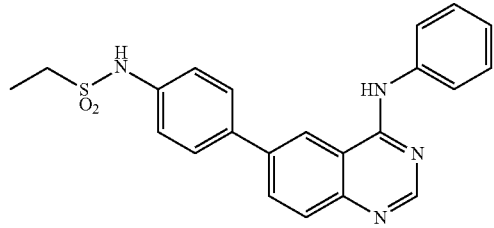 [SMILES: CCS(=O)(=O)Nc1ccc(-c2ccc3ncnc(Nc4ccccc4)c3c2)cc1]<br>N-(4-(4-(phenylamino)quinazolin-6-yl)phenyl)ethanesulfonamide |
| 25 | 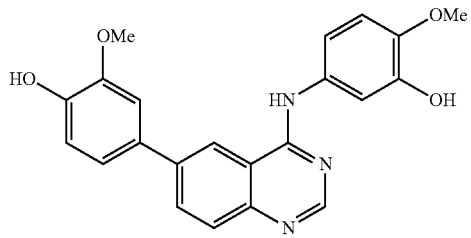 [SMILES: COc1ccc(Nc2ncnc3ccc(-c4ccc(O)c(OC)c4)cc23)cc1O]<br>4-(4-(3-hydroxy-4-methoxyphenylamino)quinazolin-6-yl)-2-methoxyphenol |
| 26 | 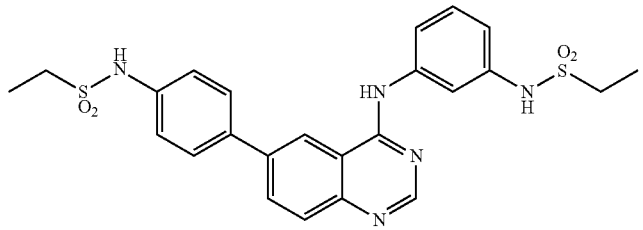 [SMILES: CCS(=O)(=O)Nc1ccc(-c2ccc3ncnc(Nc4cccc(NS(=O)(=O)CC)c4)c3c2)cc1]<br>N-(3-(6-(4-(ethylsulfonamido)phenyl)quinazolin-4-ylamino)phenyl)ethanesulfonamide |
| 27 | 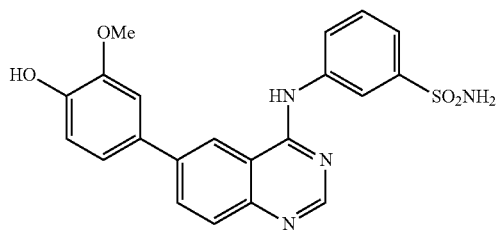 [SMILES: COc1cc(-c2ccc3ncnc(Nc4cccc(S(N)(=O)=O)c4)c3c2)ccc1O]<br>3-(6-(4-hydroxy-3-methoxyphenyl)quinazolin-4-ylamino)benzenesulfonamide |
| 28 | 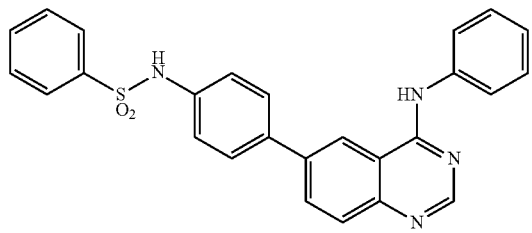 [SMILES: O=S(=O)(Nc1ccc(-c2ccc3ncnc(Nc4ccccc4)c3c2)cc1)c1ccccc1]<br>N-(4-(4-(phenylamino)quinazolin-6-yl)phenyl)benzenesulfonamide |

TABLE 1-continued

| Compd ID | Structure |
|---|---|
| 29 | 4-(4-(3-hydroxy-4-methylphenylamino)quinazolin-6-yl)-2-methoxyphenol |
| 30 | 2-methoxy-4-(7-methoxy-4-(phenylamino)quinazolin-6-yl)phenol |
| 31 | 4-(4-(3-hydroxyphenylamino)-7-methoxyquinazolin-6-yl)-2-methoxyphenol |
| 32 | 3-(6-(4-hydroxy-3-methoxyphenyl)quinazolin-4-ylamino)benzoic acid |
| 33 | 2-(6-(4-hydroxy-3-methoxyphenyl)quinazolin-4-ylamino)benzamide |

TABLE 1-continued
| Compd ID | Structure |
|---|---|
| 34 | 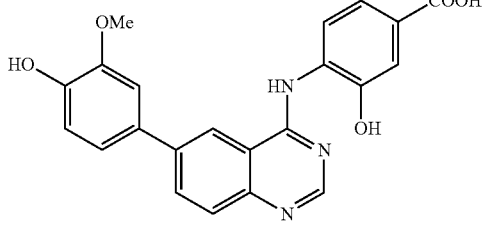<br>3-hydroxy-4-(6-(4-hydroxy-3-methoxyphenyl)quinazolin-4-ylamino)<br>benzoic acid |
| 35 | 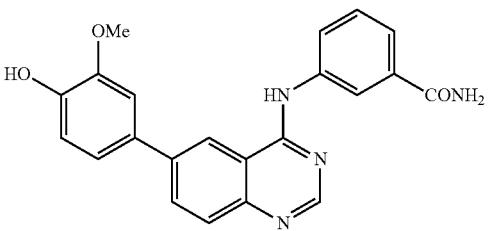 [SMILES: COc1cc(-c2ccc3ncnc(Nc4cccc(C(N)=O)c4)c3c2)ccc1O]<br>3-(6-(4-hydroxy-3-methoxyphenyl)quinazolin-4-ylamino)benzamide |
| 36 | 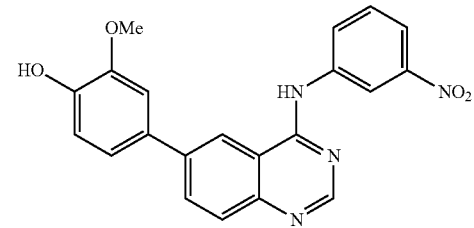<br>2-methoxy-4-(4-(3-nitrophenylamino)quinazolin-6-yl)phenol |
| 37 | 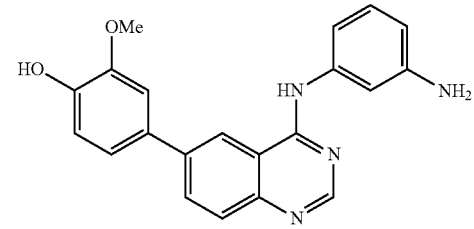 [SMILES: COc1cc(-c2ccc3ncnc(Nc4cccc([N+](=O)[O-])c4)c3c2)ccc1O]<br>4-(4-(3-aminophenylamino)quinazolin-6-yl)-2-methoxyphenol |
| 38 | 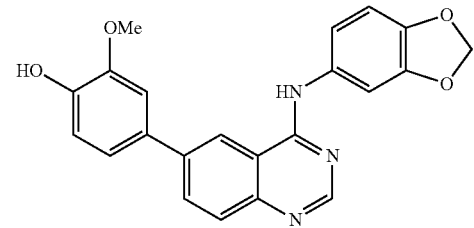 [SMILES: COc1cc(-c2ccc3ncnc(Nc4ccc5c(c4)OCO5)c3c2)ccc1O]<br>4-(4-(benzo[d][1,3]dioxol-5-ylamino)quinazolin-6-yl)-2-methoxyphenol |

TABLE 1-continued
| Compd ID | Structure |
|---|---|
| 39 | 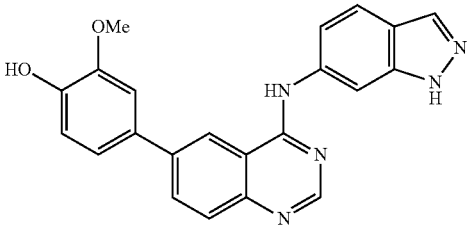 [SMILES: COc1cc(-c2ccc3ncnc(Nc4ccc5cn[nH]c5c4)c3c2)ccc1O]<br>4-(4-(1H-indazol-6-ylamino)quinazolin-6-yl)-2-methoxyphenol |
| 40 | 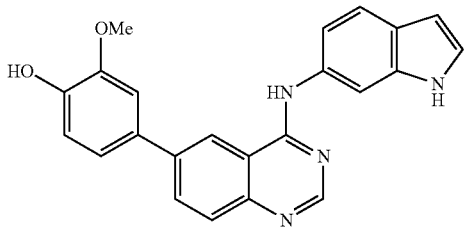 [SMILES: COc1cc(-c2ccc3ncnc(Nc4ccc5cc[nH]c5c4)c3c2)ccc1O]<br>4-(4-(1H-indol-6-ylamino)quinazolin-6-yl)-2-methoxyphenol |
| 41 | 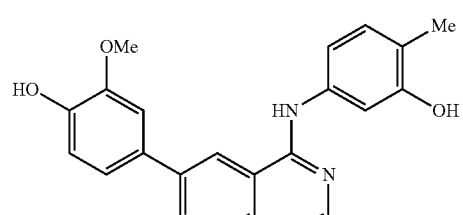<br>4-(4-(3-hydroxy-4-methylphenylamino)-7-methoxyquinazolin-6-yl)-2-methoxyphenol |
| 42 | 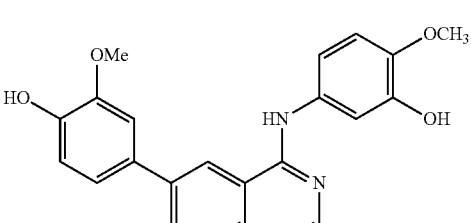<br>4-(4-(3-hydroxy-4-methoxyphenylamino)-7-methoxyquinazolin-6-yl)-2-methoxyphenol |
| 43 | 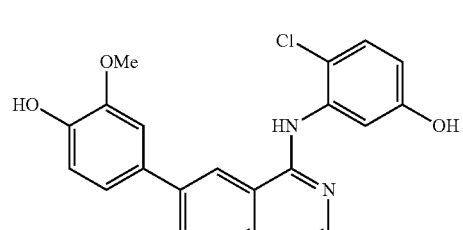<br>4-(4-(2-chloro-5-hydroxyphenylamino)-7-methoxyquinazolin-6-yl)-2-methoxyphenol |

TABLE 1-continued

| Compd ID | Structure |
|---|---|
| 44 | 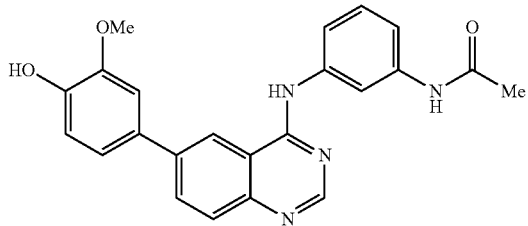 [SMILES: COc1cc(-c2ccc3ncnc(Nc4cccc(NC(C)=O)c4)c3c2)ccc1O]<br>N-(3-(6-(4-hydroxy-3-methoxyphenyl)quinazolin-4-ylamino)phenyl)acetamide |
| 45 | 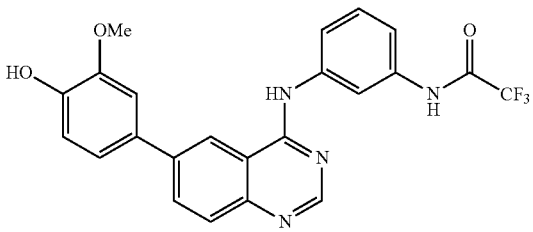 [SMILES: COc1cc(-c2ccc3ncnc(Nc4cccc(NC(=O)C(F)(F)F)c4)c3c2)ccc1O]<br>2,2,2-trifluoro-N-(3-(6-(4-hydroxy-3-methoxyphenyl)quinazolin-4-ylamino)phenyl)acetamide |
| 46 | 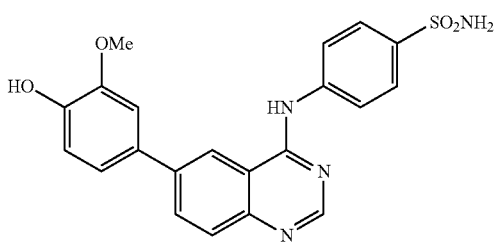 [SMILES: COc1cc(-c2ccc3ncnc(Nc4ccc(S(N)(=O)=O)cc4)c3c2)ccc1O]<br>4-(6-(4-hydroxy-3-methoxyphenyl)quinazolin-4-ylamino)benzenesulfonamide |
| 47 | 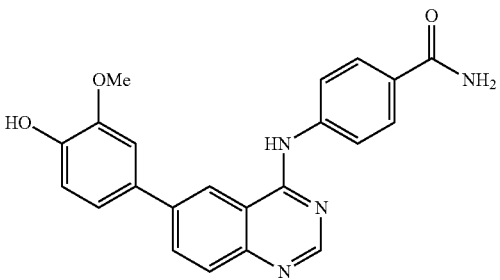 [SMILES: COc1cc(-c2ccc3ncnc(Nc4ccc(C(N)=O)cc4)c3c2)ccc1O]<br>4-(6-(4-hydroxy-3-methoxyphenyl)quinazolin-4-ylamino)benzamide |
| 48 | 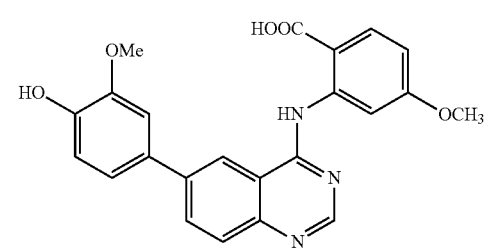 [SMILES: COc1ccc(C(=O)O)c(Nc2ncnc3ccc(-c4ccc(O)c(OC)c4)cc23)c1]<br>2-(6-(4-hydroxy-3-methoxyphenyl)quinazolin-4-ylamino)-4-methoxybenzoic acid |

TABLE 1-continued
| Compd ID | Structure |
|---|---|
| 49 | 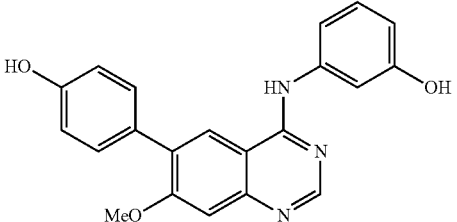 [SMILES: COc1cc2ncnc(Nc3cccc(O)c3)c2cc1-c1ccc(O)cc1]<br>3-(6-(4-hydroxyphenyl)-7-methoxyquinazolin-4-ylamino)phenol |
| 50 | 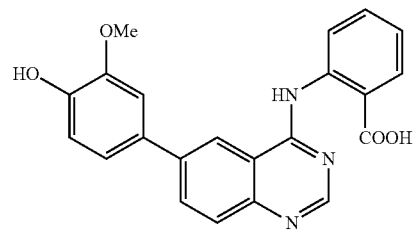 [SMILES: COc1cc(-c2ccc3ncnc(Nc4ccccc4C(=O)O)c3c2)ccc1O]<br>2-(6-(4-hydroxy-3-methoxyphenyl)quinazolin-4-ylamino)benzoic acid |
| 51 | 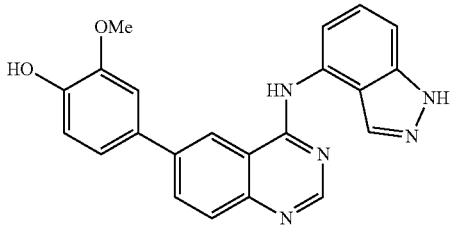 [SMILES: COc1cc(-c2ccc3ncnc(Nc4cccc5[nH]ncc45)c3c2)ccc1O]<br>4-(4-(1H-indazol-4-ylamino)quinazolin-6-yl)-2-methoxyphenol |
| 52 | 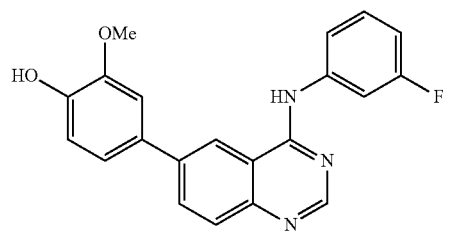 [SMILES: COc1cc(-c2ccc3ncnc(Nc4cccc(F)c4)c3c2)ccc1O]<br>4-(4-(3-fluorophenylamino)quinazolin-6-yl)-2-methoxyphenol |
| 53 | 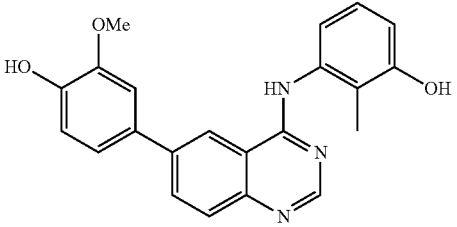 [SMILES: COc1cc(-c2ccc3ncnc(Nc4cccc(O)c4C)c3c2)ccc1O]<br>3-(6-(4-hydroxy-3-methoxyphenyl)quinazolin-4-ylamino)-2-methylphenol |

TABLE 1-continued

| Compd ID | Structure |
|---|---|
| 54 | 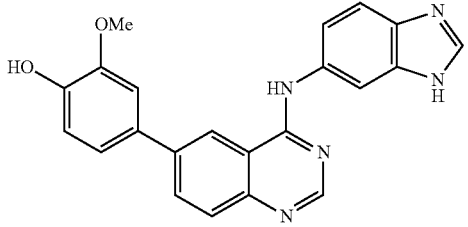 [SMILES: COc1cc(-c2ccc3ncnc(Nc4ccc5nc[nH]c5c4)c3c2)ccc1O]<br>4-(4-(1H-benzo[d]imidazol-6-ylamino)quinazolin-6-yl)-2-methoxyphenol |
| 55 | 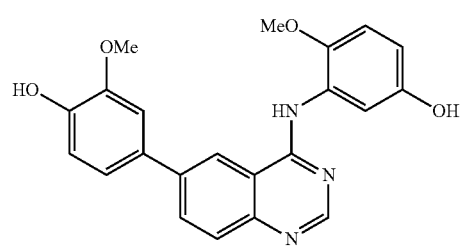 [SMILES: COc1cc(-c2ccc3ncnc(Nc4cc(O)ccc4OC)c3c2)ccc1O]<br>4-(4-(5-hydroxy-2-methoxyphenylamino)quinazolin-6-yl)-2-methoxyphenol |
| 56 | 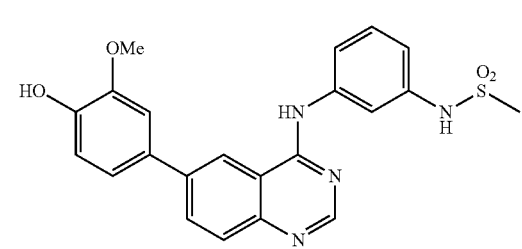 [SMILES: COc1cc(-c2ccc3ncnc(Nc4cccc(NS(C)(=O)=O)c4)c3c2)ccc1O]<br>N-(3-(6-(4-hydroxy-3-methoxyphenyl)quinazolin-4-ylamino)phenyl)methanesulfonamide |
| 57 | 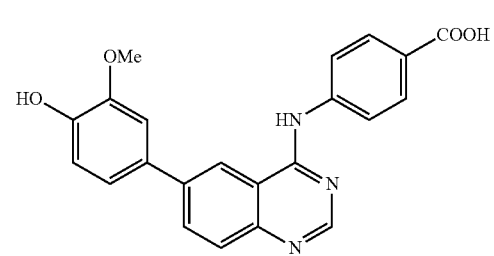 [SMILES: COc1cc(-c2ccc3ncnc(Nc4ccc(C(=O)O)cc4)c3c2)ccc1O]<br>4-(6-(4-hydroxy-3-methoxyphenyl)quinazolin-4-ylamino)benzoic acid |
| 58 | 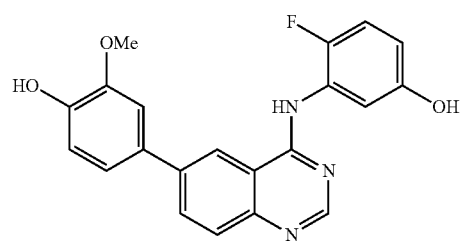 [SMILES: COc1cc(-c2ccc3ncnc(Nc4cc(O)ccc4F)c3c2)ccc1O]<br>4-(4-(2-fluoro-5-hydroxyphenylamino)quinazolin-6-yl)-2-methoxyphenol |

TABLE 1-continued
| Compd ID | Structure |
|---|---|
| 59 | 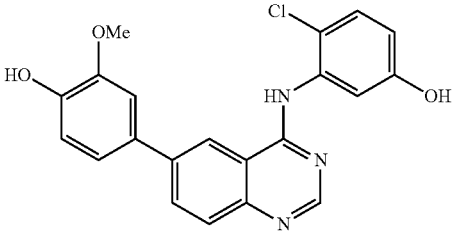 [SMILES: COc1cc(-c2ccc3ncnc(Nc4cc(O)ccc4Cl)c3c2)ccc1O]<br>4-(4-(2-chloro-5-hydroxyphenylamino)quinazolin-6-yl)-2-methoxyphenol |
| 60 | 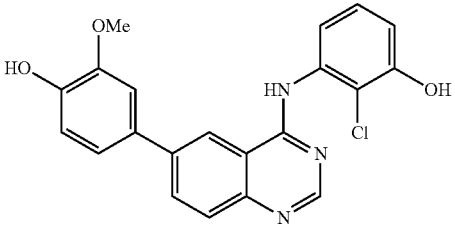 [SMILES: COc1cc(-c2ccc3ncnc(Nc4cccc(O)c4Cl)c3c2)ccc1O]<br>2-chloro-3-(6-(4-hydroxy-3-methoxyphenyl)quinazolin-4-ylamino)phenol |
| 61 | 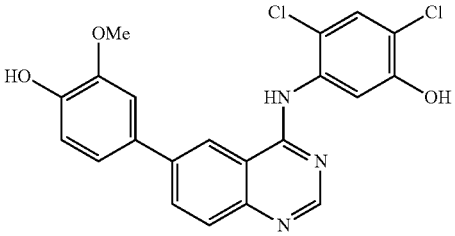<br>2,4-dichloro-5-(6-(4-hydroxy-3-methoxyphenyl)quinazolin-4-ylamino)phenol |
| 62 | 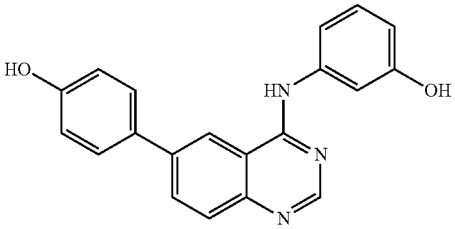 [SMILES: Oc1ccc(-c2ccc3ncnc(Nc4cccc(O)c4)c3c2)cc1]<br>3-(6-(4-hydroxyphenyl)quinazolin-4-ylamino)phenol |
| 63 | 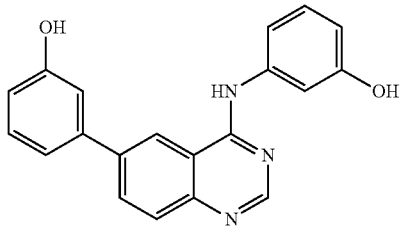 [SMILES: Oc1cccc(Nc2ncnc3ccc(-c4cccc(O)c4)cc23)c1]<br>3-(6-(3-hydroxyphenyl)quinazolin-4-ylamino)phenol |

TABLE 1-continued
| Compd ID | Structure |
|---|---|
| 64 | 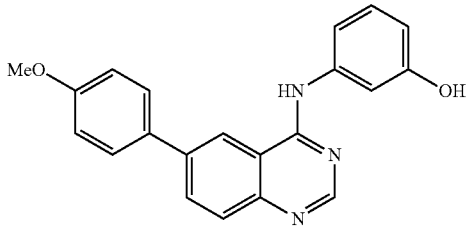 [SMILES: COc1ccc(-c2ccc3ncnc(Nc4cccc(O)c4)c3c2)cc1]<br>3-(6-(4-methoxyphenyl)quinazolin-4-ylamino)phenol |
| 65 | 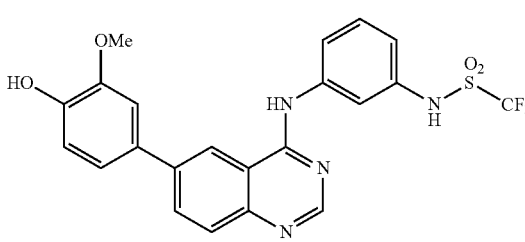<br>1,1,1-trifluoro-N-(3-(6-(4-hydroxy-3-methoxyphenyl)quinazolin-4-ylamino)phenyl)methanesulfonamide |
| 66 | 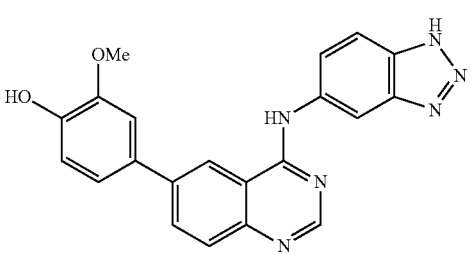 [SMILES: COc1cc(-c2ccc3ncnc(Nc4ccc5[nH]nnc5c4)c3c2)ccc1O]<br>4-(4-(1H-benzo[d][1,2,3]triazol-5-ylamino)quinazolin-6-yl)-2-methoxyphenol |
| 67 | 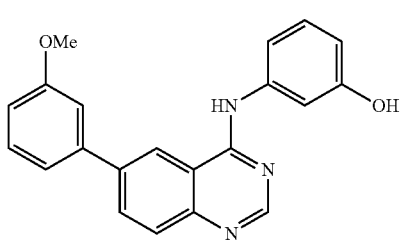 [SMILES: COc1cccc(-c2ccc3ncnc(Nc4cccc(O)c4)c3c2)c1]<br>3-(6-(3-methoxyphenyl)quinazolin-4-ylamino)phenol |
| 68 | 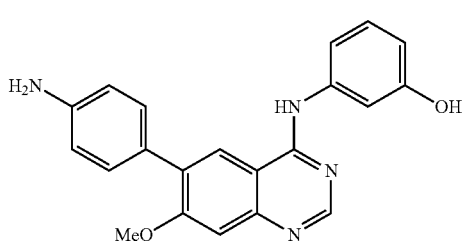 [SMILES: COc1cc2ncnc(Nc3cccc(O)c3)c2cc1-c1ccc(N)cc1]<br>3-(6-(4-aminophenyl)-7-methoxyquinazolin-4-ylamino)phenol |

TABLE 1-continued
| Compd ID | Structure |
|---|---|
| 69 | 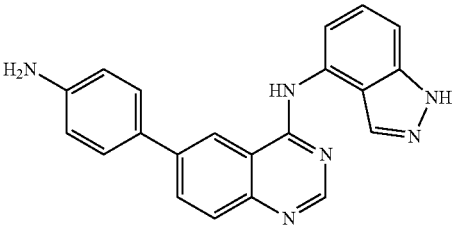<br>6-(4-aminophenyl)-N-(1H-indazol-4-yl)quinazolin-4-amine |
| 70 | 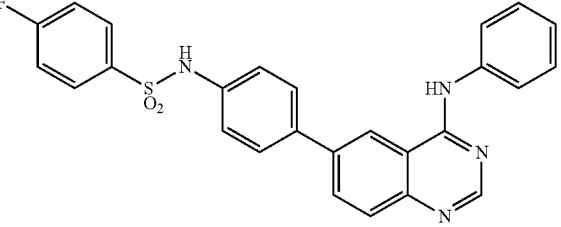<br>4-fluoro-N-(4-(4-(phenylamino)quinazolin-6-yl)phenyl)<br>benzenesulfonamide |
| 71 | 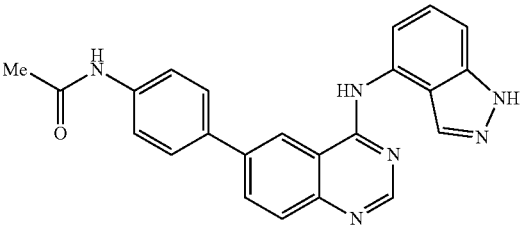 [SMILES: CC(=O)Nc1ccc(-c2ccc3ncnc(Nc4cccc5[nH]ncc45)c3c2)cc1]<br>N-(4-(4-(1H-indazol-4-ylamino)quinazolin-6-yl)phenyl)acetamide |
| 72 | 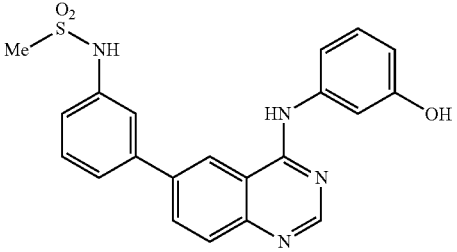 [SMILES: CS(=O)(=O)Nc1cccc(-c2ccc3ncnc(Nc4cccc(O)c4)c3c2)c1]<br>N-(3-(4-(3-hydroxyphenylamino)quinazolin-6-yl)phenyl)<br>methanesulfonamide |
| 73 | 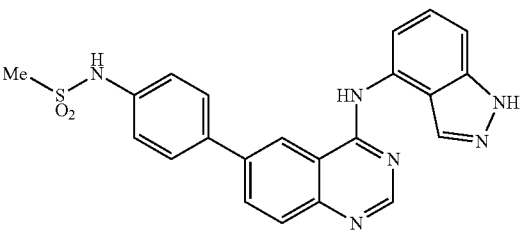 [SMILES: CS(=O)(=O)Nc1ccc(-c2ccc3ncnc(Nc4cccc5[nH]ncc45)c3c2)cc1]<br>N-(4-(4-(1H-indazol-4-ylamino)quinazolin-6-yl)phenyl)<br>methanesulfonamide |

TABLE 1-continued

| Compd ID | Structure |
|---|---|
| 74 | 6-(2-fluoro-3-methoxyphenyl)-N-(1H-indazol-4-yl)quinazolin-4-amine |
| 75 | 6-(3-fluoro-4-methoxyphenyl)-N-(1H-indazol-4-yl)quinazolin-4-amine |
| 76 | 6-(3-chloro-4-methoxyphenyl)-N-(1H-indazol-4-yl)quinazolin-4-amine |
| 77 | N-(1H-indazol-4-yl)-6-(4-methoxy-2-methylphenyl)quinazolin-4-amine |
| 78 | N-(1H-indazol-4-yl)-6-(4-methoxy-3-methylphenyl)quinazolin-4-amine |

TABLE 1-continued

| Compd ID | Structure |
|---|---|
| 79 | 6-(3-chloro-4-fluorophenyl)-N-(1H-indazol-4-yl)quinazolin-4-amine |
| 80 | 6-(4-chlorophenyl)-N-(1H-indazol-4-yl)quinazolin-4-amine |
| 81 | 6-(3-fluorophenyl)-N-(1H-indazol-4-yl)quinazolin-4-amine |
| 82 | 4-(4-(1H-benzo[d][1,2,3]triazol-4-ylamino)quinazolin-6-yl)-2-methoxyphenol |
| 83 | 4-(4-(1H-indol-4-ylamino)quinazolin-6-yl)-2-methoxyphenol |

TABLE 1-continued

| Compd ID | Structure |
|---|---|
| 84 | 6-(4-fluoro-3-methoxyphenyl)-N-(1H-indazol-4-yl)quinazolin-4-amine |
| 85 | 6-(3,4-difluorophenyl)-N-(1H-indazol-4-yl)quinazolin-4-amine |
| 86 | N-(1H-indazol-4-yl)-6-phenylquinazolin-4-amine |
| 87 | N-(1H-indazol-4-yl)-6-(3-(trifluoromethyl)phenyl)quinazolin-4-amine |
| 88 | 4-(4-(1H-indazol-4-ylamino)quinazolin-6-yl)benzonitrile |

TABLE 1-continued
| Compd ID | Structure |
|---|---|
| 89 | 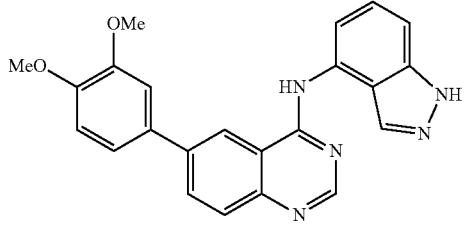 [SMILES: COc1ccc(-c2ccc3ncnc(Nc4cccc5[nH]ncc45)c3c2)cc1OC]<br>6-(3,4-dimethoxyphenyl)-N-(1H-indazol-4-yl)quinazolin-4-amine |
| 90 | 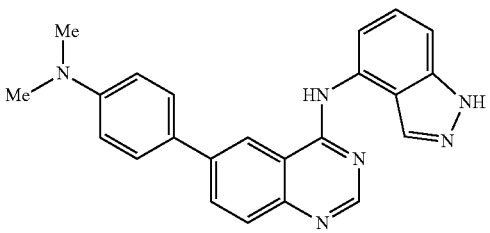 [SMILES: CN(C)c1ccc(-c2ccc3ncnc(Nc4cccc5[nH]ncc45)c3c2)cc1]<br>6-(4-(dimethylamino)phenyl)-N-(1H-indazol-4-yl)quinazolin-4-amine |
| 91 | 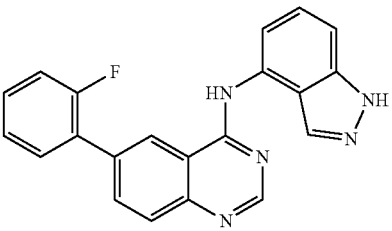 [SMILES: Fc1ccccc1-c1ccc2ncnc(Nc3cccc4[nH]ncc34)c2c1]<br>6-(2-fluorophenyl)-N-(1H-indazol-4-yl)quinazolin-4-amine |
| 92 | 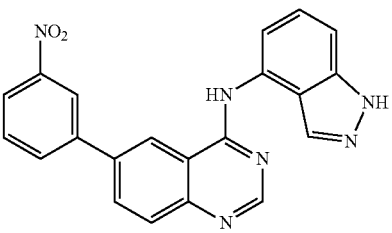 [SMILES: O=[N+]([O-])c1cccc(-c2ccc3ncnc(Nc4cccc5[nH]ncc45)c3c2)c1]<br>N-(1H-indazol-4-yl)-6-(3-nitrophenyl)quinazolin-4-amine |
| 93 | 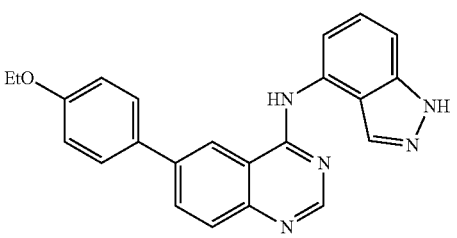<br>6-(4-ethoxyphenyl)-N-(1H-indazol-4-yl)quinazolin-4-amine |

TABLE 1-continued

| Compd ID | Structure |
|---|---|
| 94 | (3-(4-(1H-indazol-4-ylamino)quinazolin-6-yl)phenyl)methanol |
| 95 | N-(3-(4-(1H-indazol-4-ylamino)quinazolin-6-yl)phenyl) methanesulfonamide |
| 96 | 6-(benzo[d][1,3]dioxol-5-yl)-N-(1H-indazol-4-yl)quinazolin-4-amine |
| 97 | 3-(4-(1H-indazol-4-ylamino)quinazolin-6-yl)benzamide |
| 98 | 5-(4-(1H-indazol-4-ylamino)quinazolin-6-yl)-2-methoxybenzaldehyde |

TABLE 1-continued
| Compd ID | Structure |
|---|---|
| 99 | 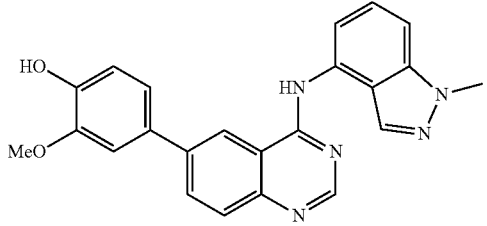 [SMILES: COc1cc(-c2ccc3ncnc(Nc4cccc5c4cnn5C)c3c2)ccc1O]<br>2-methoxy-4-(4-(1-methyl-1H-indazol-4-ylamino)quinazolin-6-yl)phenol |
| 100 | 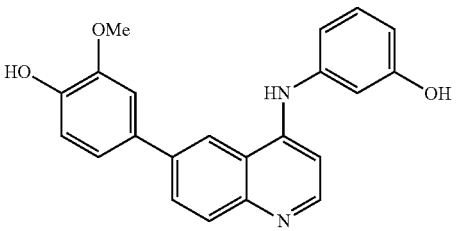 [SMILES: COc1cc(-c2ccc3nccc(Nc4cccc(O)c4)c3c2)ccc1O]<br>4-(4-(3-hydroxyphenylamino)quinolin-6-yl)-2-methoxyphenol |
| 101 | 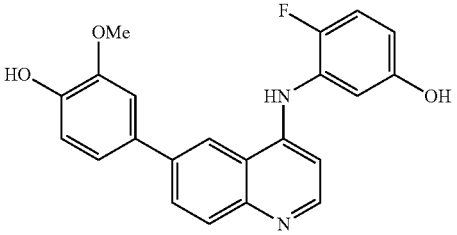 [SMILES: COc1cc(-c2ccc3nccc(Nc4cc(O)ccc4F)c3c2)ccc1O]<br>4-(4-(2-fluoro-5-hydroxyphenylamino)quinolin-6-yl)-2-methoxyphenol |
| 102 | 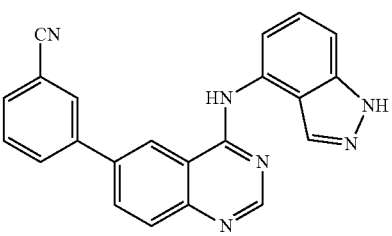 [SMILES: N#Cc1cccc(-c2ccc3ncnc(Nc4cccc5[nH]ncc45)c3c2)c1]<br>3-(4-(1H-indazol-4-ylamino)quinazolin-6-yl)benzonitrile |
| 103 | 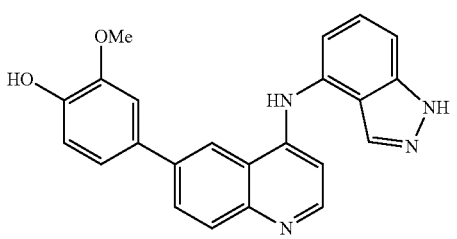 [SMILES: COc1cc(-c2ccc3nccc(Nc4cccc5[nH]ncc45)c3c2)ccc1O]<br>4-(4-(1H-indazol-4-ylamino)quinolin-6-yl)-2-methoxyphenol |

TABLE 1-continued

| Compd ID | Structure |
|---|---|
| 104 | 6-(5-fluoro-2-methylphenyl)-N-(1H-indazol-4-yl)quinazolin-4-amine |
| 105 | 6-(2,3-dimethoxyphenyl)-N-(1H-indazol-4-yl)quinazolin-4-amine |
| 106 | 3-(6-(4-(dimethylamino)phenyl)quinazolin-4-ylamino)phenol |
| 107 | 4-(4-(1H-indazol-4-ylamino)quinazolin-6-yl)benzenesulfonamide |
| 108 | N-(3-(4-(1H-indazol-4-ylamino)quinazolin-6-yl)phenyl)ethanesulfonamide |

TABLE 1-continued
| Compd ID | Structure |
|---|---|
| 109 | 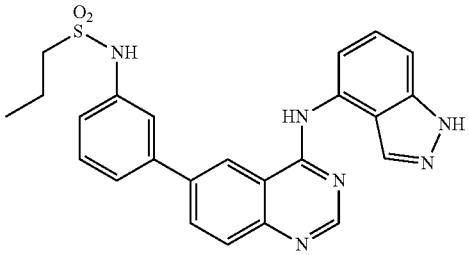 [SMILES: CCCS(=O)(=O)Nc1cccc(-c2ccc3ncnc(Nc4cccc5[nH]ncc45)c3c2)c1]<br>N-(3-(4-(1H-indazol-4-ylamino)quinazolin-6-yl)phenyl)propane-1-sulfonamide |
| 110 | 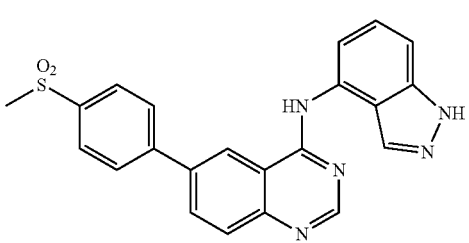 [SMILES: CS(=O)(=O)c1ccc(-c2ccc3ncnc(Nc4cccc5[nH]ncc45)c3c2)cc1]<br>N-(1H-indazol-4-yl)-6-(4-(methylsulfonyl)phenyl)quinazolin-4-amine |
| 111 | 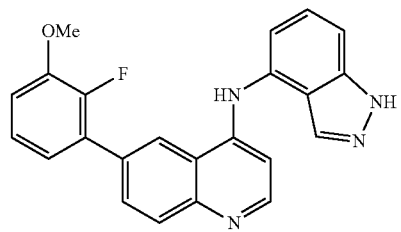 [SMILES: COc1cccc(-c2ccc3nccc(Nc4cccc5[nH]ncc45)c3c2)c1F]<br>6-(2-fluoro-3-methoxyphenyl)-N-(1H-indazol-4-yl)quinolin-4-amine |
| 112 | 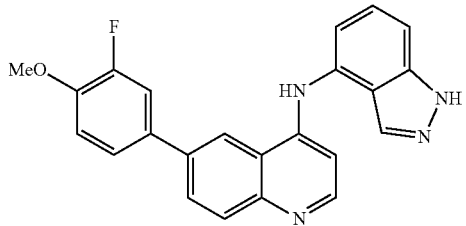 [SMILES: COc1ccc(-c2ccc3nccc(Nc4cccc5[nH]ncc45)c3c2)cc1F]<br>6-(3-fluoro-4-methoxyphenyl)-N-(1H-indazol-4-yl)quinolin-4-amine |
| 113 | 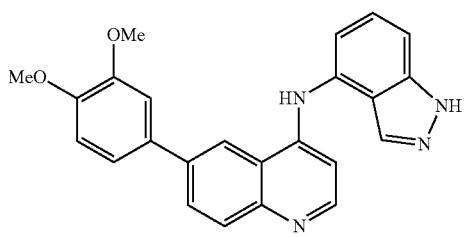 [SMILES: COc1ccc(-c2ccc3nccc(Nc4cccc5[nH]ncc45)c3c2)cc1OC]<br>6-(3,4-dimethoxyphenyl)-N-(1H-indazol-4-yl)quinolin-4-amine |

TABLE 1-continued

| Compd ID | Structure |
|---|---|
| 114 | 3-(4-(1H-indazol-4-ylamino)quinolin-6-yl)benzonitrile |
| 115 | 6-(3-chloro-4-methoxyphenyl)-N-(1H-indazol-4-yl)quinolin-4-amine |
| 116 | 5-(4-(1H-indazol-4-ylamino)quinolin-6-yl)-2-methoxybenzaldehyde |
| 117 | 3-(4-(1H-indazol-4-ylamino)quinolin-6-yl)benzamide |
| 118 | 4-(4-(3-(difluoromethoxy)phenylamino)quinazolin-6-yl)-2-methoxyphenol |

TABLE 1-continued

| Compd ID | Structure |
|---|---|
| 119 | 4-(4-(2-fluorophenylamino)quinazolin-6-yl)-2-methoxyphenol |
| 120 | N-(1H-indazol-4-yl)-6-(4-(methylsulfonyl)phenyl)quinolin-4-amine |
| 121 | 6-(4-aminophenyl)-N-(1H-indazol-4-yl)quinolin-4-amine |
| 122 | N-(3-(4-(1H-indazol-4-ylamino)quinolin-6-yl)phenyl)propane-1-sulfonamide |
| 123 | N-(1H-indazol-4-yl)-6-(3-methoxyphenyl)quinolin-4-amine |

TABLE 1-continued
| Compd ID | Structure |
|---|---|
| 124 | 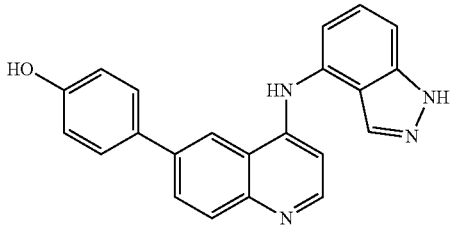<br>4-(4-(1H-indazol-4-ylamino)quinolin-6-yl)phenol |
| 125 | 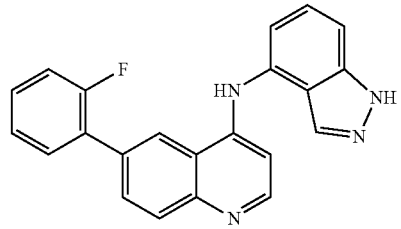 [SMILES: Fc1ccccc1-c1ccc2nccc(Nc3cccc4[nH]ncc34)c2c1]<br>6-(2-fluorophenyl)-N-(1H-indazol-4-yl)quinolin-4-amine |
| 126 | 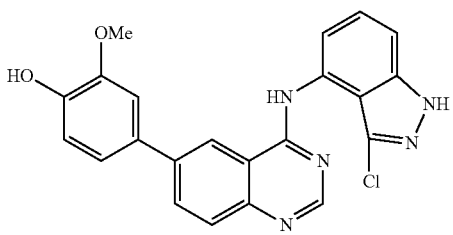 [SMILES: COc1cc(-c2ccc3ncnc(Nc4cccc5[nH]nc(Cl)c45)c3c2)ccc1O]<br>4-(4-(3-chloro-1H-indazol-4-ylamino)quinazolin-6-yl)-2-methoxyphenol |
| 127 | 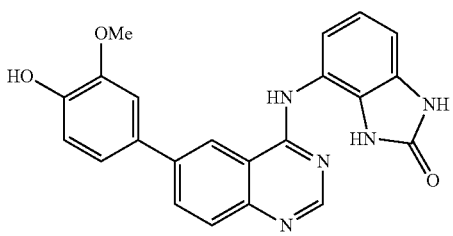 [SMILES: COc1cc(-c2ccc3ncnc(Nc4cccc5[nH]c(=O)[nH]c45)c3c2)ccc1O]<br>4-(6-(4-hydroxy-3-methoxyphenyl)quinazolin-4-ylamino)-1H-benzo[d]imidazol-2(3H)-one |
| 128 | 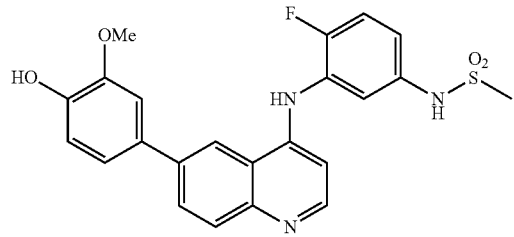 [SMILES: COc1cc(-c2ccc3nccc(Nc4cc(NS(C)(=O)=O)ccc4F)c3c2)ccc1O]<br>N-(4-fluoro-3-(6-(4-hydroxy-3-methoxyphenyl)quinolin-4-ylamino)phenyl)methanesulfonamide |

TABLE 1-continued

| Compd ID | Structure |
|---|---|
| 129 | N-(4-fluoro-3-(6-(4-hydroxy-3-methoxyphenyl)quinazolin-4-ylamino)phenyl)methanesulfonamide |
| 130 | N-(2-fluoro-5-(6-(4-hydroxy-3-methoxyphenyl)quinazolin-4-ylamino)phenyl)methanesulfonamide |
| 131 | 4-(4-(1H-indazol-4-ylamino)quinazolin-6-yl)phenol |
| 132 | N,6-diphenylquinazolin-4-amine |
| 133 | 3-(6-phenylquinazolin-4-ylamino)phenol |

TABLE 1-continued

| Compd ID | Structure |
|---|---|
| 134 | 4-(4-(2,6-difluorophenylamino)quinazolin-6-yl)-2-methoxyphenol |
| 135 | 4-(1H-indazol-4-ylamino)-6-(4-hydroxy-3-methoxyphenyl) quinoline-3-carbonitrile |
| 136 | 4-(4-(5-fluoro-1H-indazol-4-ylamino)quinazolin-6-yl)-2-methoxyphenol |
| 137 | 6-(5-amino-2-fluorophenyl)-N-(1H-indazol-4-yl)quinolin-4-amine |
| 138 | 6-(5-amino-2-fluorophenyl)-N-(1H-indazol-4-yl)quinolin-4-amine |

TABLE 1-continued

| Compd ID | Structure |
|---|---|
| 139 | 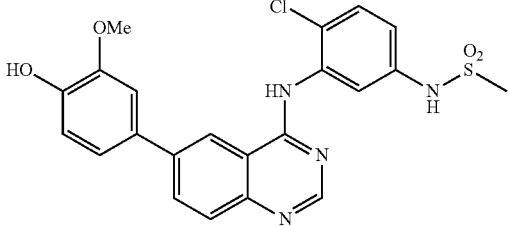 [SMILES: COc1cc(-c2ccc3ncnc(Nc4cc(NS(C)(=O)=O)ccc4F)c3c2)ccc1O]<br>N-(4-chloro-3-(6-(4-hydroxy-3-methoxyphenyl)quinazolin-4-ylamino)phenyl)methanesulfonamide |
| 140 | 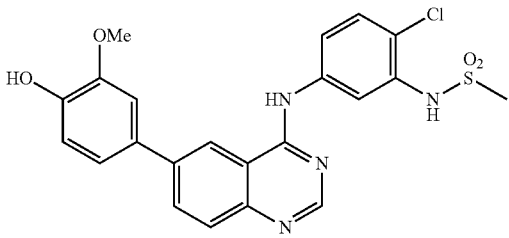<br>N-(2-chloro-5-(6-(4-hydroxy-3-methoxyphenyl)quinazolin-4-ylamino)phenyl)methanesulfonamide |
| 141 | 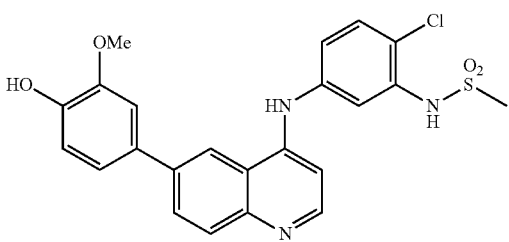 [SMILES: COc1cc(-c2ccc3nccc(Nc4ccc(Cl)c(NS(C)(=O)=O)c4)c3c2)ccc1O]<br>N-(2-chloro-5-(6-(4-hydroxy-3-methoxyphenyl)quinolin-4-ylamino)phenyl)methanesulfonamide |
| 142 | 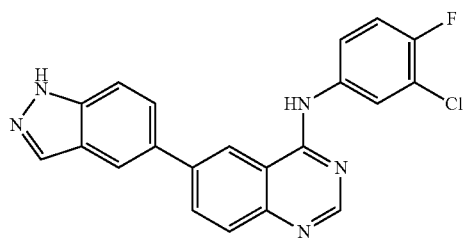 [SMILES: Fc1ccc(Nc2ncnc3ccc(-c4ccc5[nH]ncc5c4)cc23)cc1Cl]<br>N-(3-chloro-4-fluorophenyl)-6-(1H-indazol-5-yl)quinazolin-4-amine |
| 143 | 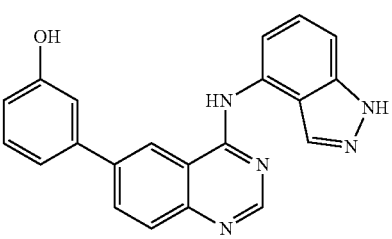 [SMILES: Oc1cccc(-c2ccc3ncnc(Nc4cccc5[nH]ncc45)c3c2)c1]<br>3-(4-(1H-indazol-4-ylamino)quinazolin-6-yl)phenol |

TABLE 1-continued

| Compd ID | Structure |
|---|---|
| 144 | N-(1H-indazol-4-yl)-6-(3-methoxyphenyl)quinazolin-4-amine |
| 145 | N-(2-fluoro-5-(6-(4-hydroxy-3-methoxyphenyl)quinolin-4-ylamino)phenyl)methanesulfonamide |
| 146 | N-(1H-indazol-4-yl)-6-(3-methoxyphenyl)quinolin-4-amine |
| 147 | N-(1H-indazol-4-yl)-6-(4-methoxyphenyl)quinazolin-4-amine |
| 148 | 3-(4-(1H-indazol-4-ylamino)quinolin-6-yl)phenol |

TABLE 1-continued

| Compd ID | Structure |
|---|---|
| 149 | 4-(4-(5-fluoro-1H-indazol-4-ylamino)quinazolin-6-yl)-2-methoxyphenol |
| 150 | N-(2,4-difluoro-5-(6-(4-hydroxy-3-methoxyphenyl)quinazolin-4-ylamino)phenyl)methanesulfonamide |
| 151 | N-(3-ethynylphenyl)-6-(4-methoxyphenyl)quinazolin-4-amine |
| 152 | 3-(6-(4-methoxyphenyl)quinazolin-4-yloxy)phenol |
| 153 | N-(1H-indazol-4-yl)-6-(1H-indazol-5-yl)quinazolin-4-amine |

TABLE 1-continued

| Compd ID | Structure |
|---|---|
| 154 | 4-(4-(5-hydroxy-2-methylphenylamino)quinazolin-6-yl)-2-methoxyphenol |
| 155 | 2-methoxy-4-(4-(5-methyl-1H-indazol-4-ylamino)quinazolin-6-yl)phenol |
| 156 | 4-fluoro-5-(6-(4-hydroxy-3-methoxyphenyl)quinazolin-4-ylamino)-2-methylphenol |
| 157 | 4-(4-(4-chloro-3-hydroxyphenylamino)quinazolin-6-yl)-2-methoxyphenol |
| 158 | 2,4-difluoro-5-(6-(4-hydroxy-3-methoxyphenyl)quinazolin-4-ylamino)phenol |

TABLE 1-continued
| Compd ID | Structure |
|---|---|
| 159 | 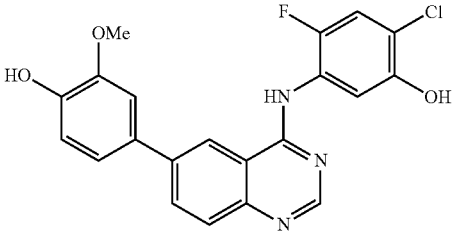 [SMILES: COc1cc(-c2ccc3ncnc(Nc4cc(O)c(Cl)cc4F)c3c2)ccc1O]<br>2-chloro-4-fluoro-5-(6-(4-hydroxy-3-methoxyphenyl)<br>quinazolin-4-ylamino)phenol |
| 160 | 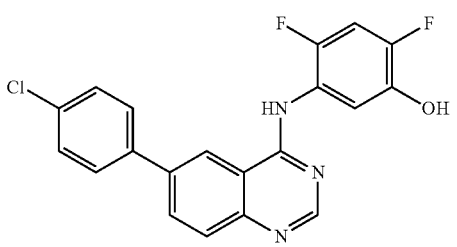 [SMILES: Oc1cc(Nc2ncnc3ccc(-c4ccc(Cl)cc4)cc23)c(F)cc1F]<br>5-(6-(4-chlorophenyl)quinazolin-4-ylamino)-2,4-difluorophenol |
| 161 | 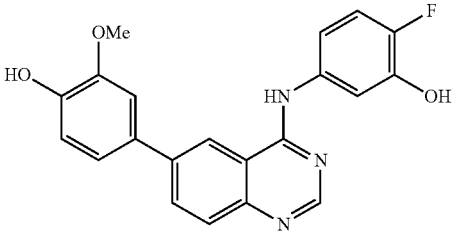 [SMILES: COc1cc(-c2ccc3ncnc(Nc4ccc(F)c(O)c4)c3c2)ccc1O]<br>4-(4-(4-fluoro-3-hydroxyphenylamino)quinazolin-6-yl)-2-methoxyphenol |
| 162 | 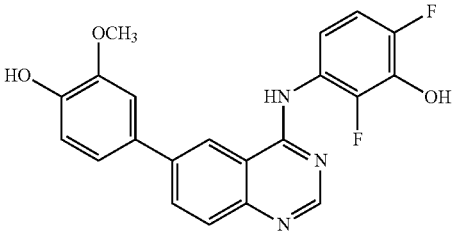 [SMILES: COc1cc(-c2ccc3ncnc(Nc4ccc(F)c(O)c4F)c3c2)ccc1O]<br>2,6-difluoro-3-(6-(4-hydroxy-3-methoxyphenyl)<br>quinazolin-4-ylamino)phenol |
| 163 | 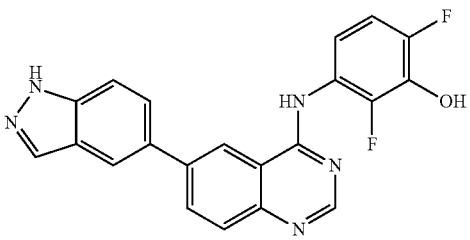 [SMILES: Oc1c(F)ccc(Nc2ncnc3ccc(-c4ccc5[nH]ncc5c4)cc23)c1F]<br>3-(6-(1H-indazol-5-yl)quinazolin-4-ylamino)-2,6-difluorophenol |

TABLE 1-continued

| Compd ID | Structure |
|---|---|
| 164 | 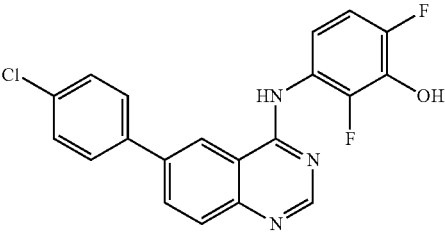 [SMILES: Oc1c(F)ccc(Nc2ncnc3ccc(-c4ccc(Cl)cc4)cc23)c1F]<br>3-(6-(4-chlorophenyl)quinazolin-4-ylamino)-2,6-difluorophenol |

As noted above, the quinazoline compounds of this invention can be prepared by conventional chemical transformations (including protecting group methodologies). One of ordinary skill in the art would be able to prepare these compounds without inventive efforts. For example, such reactions are described in R. Larock, *Comprehensive Organic Transformations*, VCH Publishers (1989); T. W. Greene and P. G. M. Wuts, *Protective Groups in Organic Synthesis*, 3rd Ed., John Wiley and Sons (1999); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Based on the conventional synthetic reactions, one skilled in the art would know how to prepare these quinazoline compounds without undue experimentation or inventive efforts. For example, synthetic Scheme I illustrates an exemplary synthesis of the quinazoline compounds of the present invention.

Scheme 1

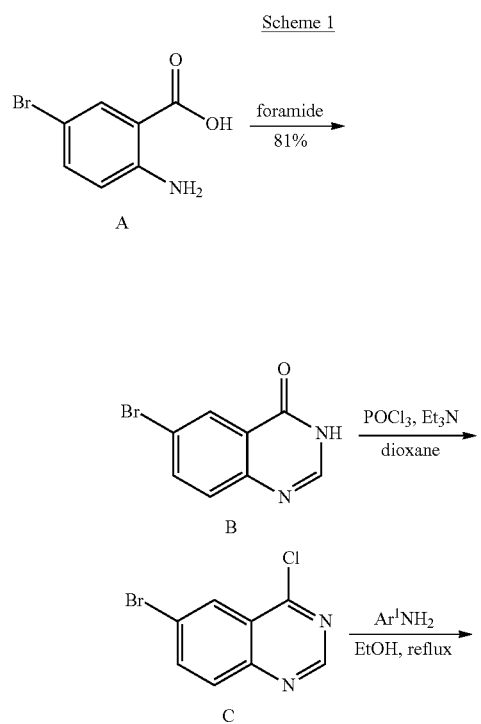

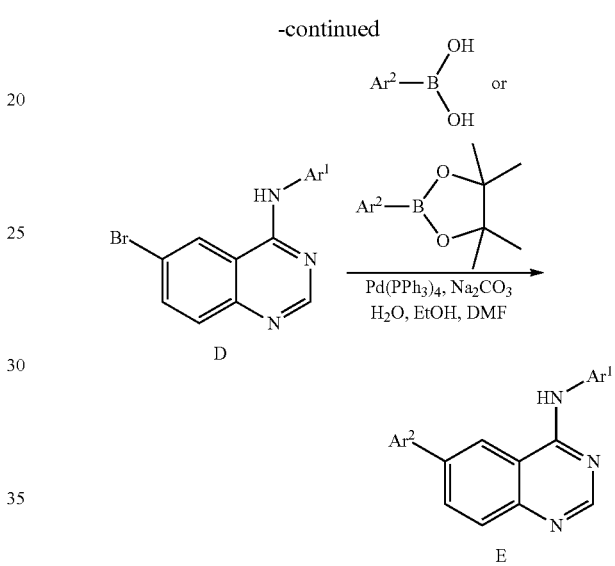

Briefly, 2-amino-5-bromobenzoic acid (A, 50.0 g, 0.233 mmol, 1.0 equiv) is added to formamide (50.0 mL, d=1.133, 56.7 g, 1.26 mmol). The reaction mixture is heated at reflux for 12 h. The solution is then cooled to 70° C., and EtOH (100 mL) is added to the reaction mixture. The resultant precipitates are collected by filtration, washed with EtOH (50 mL), and dried under vacuum to provide the desired 6-bromo-3H-quinazolin-4-one (B, 42.5 g, 0.189 mol) in 81% yield: ESI-MS m/z 225.0 $(M+H)^+$.

Next, to a dioxane solution containing 6-bromo-3H-quinazolin-4-one (B, 15.0 g, 66.7 mmol, 1.0 equiv) is added $POCl_3$ (20.0 mL, d=1.67, 33.4 g, 219 mmol, 3.3 equiv). $Et_3N$ (30.0 mL, d=0.726, 21.8 g, 215 mmol) is then added dropwise to the solution. The reaction mixture is heated at reflux for 12 h. The solution is cooled to room temperature and poured into an ice-water mixture. Then, the resultant precipitate is collected by filtration, washed with $H_2O$ (100 mL), and dried under vacuum to provide the desired 6-bromo-4-chloroquinazoline (C, 15.4 g, 63.2 mmol) in 95% yield: ESI-MS m/z 243.0 $(M+H)^+$.

To an EtOH solution of 6-bromo-4-chloroquinazoline (C, 1.0 equiv) is added arylamine ($Ar^1NH_2$, 1.5 equiv). The reaction mixture is heated at reflux for 12 h. The solution was cooled, and the resultant solids are collected by filtration, washed with EtOH, and dried under vacuum to provide the desired 4-arylamino-6-bromoquinazoline (D).

A mixture of 4-arylamino-6-bromoquinazoline (D, 1.0 equiv) and $Pd(PPh_3)_4$ (0.10 equiv) in DMF/EtOH solution (4:1) is added with arylboronic acid (1.5 equiv) or 4,4,5,5-tetramethyl-2-aryl-1,3,2-dioxaborolane (1.5 equiv) with aqueous $Na_2CO_3$ (2.0 M, 2.0 equiv). The reaction mixture is heated at reflux for 12 h. The solution is filtered through Celite, and the filtrate is collected. Cold $H_2O$ is added to the filtrate until the precipitate formed. The solids are collected, washed with $CH_2Cl_2$ and MeOH, and dried under vacuum to provide the desired 4-arylamino-6-arylquinazoline (E).

A quinazoline compound thus synthesized can be further purified by any suitable purification techniques, such as flash column chromatography, high performance liquid chromatography, crystallization, or any other suitable methods.

The above synthetic Scheme illustrates general procedures for the preparation of quinazoline compounds of the invention. One of ordinary skill in the art would appreciate that these reactions are common organic reactions and can be carried out without undue experimentation. One of ordinary skill would also appreciate that various $Ar^1$ and $Ar^2$ in Scheme 1 may be used to provide the desired substitutions. Furthermore, the reagents used for these syntheses are commercially available from various sources, including Sigma-Adrich, Acros Co., TCI, Merck, and Alfa.

The quinazoline compounds described herein may contain a non-aromatic double bond and one or more asymmetric centers. Thus, they can occur as stereoisomers, such as racemates and racemic mixtures, single enantiomers, individual diastereomers, diastereomeric mixtures, and cis- or trans-isomeric forms. All such isomeric forms are within the scope of the invention.

Also within the scope of this invention are (1) pharmaceutical compositions that each contain an effective amount of at least one of the quinazoline compounds of this invention and a pharmaceutically acceptable carrier, (2) methods for treating protein kinase-related diseases (e.g., cancer) by administering to a subject in need of this treatment an effective amount of a quinazoline compound of the invention, and (3) methods of decreasing the activity of at least one protein kinase by contacting the at least one protein kinase with at least one of the quinazoline compounds of this invention.

Compounds of the invention can be used to treat kinase-related diseases or conditions, such as cancers. Cancers or tumors that can be treated by the methods of the invention include any abnormal cell or tissue growth, whether malignant, pre-malignant, or non-malignant. These diseases are characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term "cancer" includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovarian cancer, uterine body cancer, cervical cancer, oral cancer, skin cancer, brain cancer, lymphoma, and leukemia. It also includes drug resistant cancer (including but not limited to multidrug resistant cancer).

The compounds described herein may be administered to a mammal, optionally in conjunction with radiation therapy, immunotherapy, monoclonal antibody therapy, hormonal therapy, chemotherapy using other agents, and/or surgery. By in conjunction with, the therapies need not occur at the same time, but can be in succession, or alternating with each other and/or periods of rest and recovery.

In accordance with one or more embodiments of the invention, a protein kinase-related disease, such as cancer, may be treated with a method comprising administering an effective amount of at least one quinazoline compound of this invention, optionally with at least one chemotherapeutic agent to a mammal. Nonlimiting examples of chemotherapeutic agents include, PK inhibitors other than the compound described herein (e.g., imatinib mesylate, gefitinib, dasatinib, erlotinib, lapatinib, sunitinib, nilotinib, and sorafenib; antibodies, including, e.g., trastuzumab, rituximab, cetuximab, and bevacizumab; mitoxantrone; dexamethasone; prednisone; and temozolomide), alkylating agents (e.g., melphalan, chlorambucil, busulfan, thiotepa, ifosfamide, carmustine, lomustine, semustine, streptozocin, decarbazine, and cyclophosphamide), mitotic inhibitors, antimetabolites (e.g., capecitibine, gemcitabine, 5-fluorouracil or 5-fluorouracil/leucovorin, fludarabine, cytarabine, mercaptopurine, thioguanine, pentostatin, and methotrexate), cell cycle inhibitors, enzymes, hormones, anti-hormones, growth-factor inhibitors, plant alkaloids and terpenoids, topoisomerase inhibitors (e.g., etoposide, teniposide, camptothecin, topotecan, irinotecan, doxorubicin, and daunorubicin), antitumor antibiotics (e.g., actinomycin D, bleomycin, mitomycin C, adriamycin, daunorubicin, idarubicin, doxorubicin and pegylated liposomal doxorubicin), vinca alkaloids (e.g., vincristine and vinblastin), taxanes (e.g., paclitaxel and docetaxel), platinum agents (e.g., cisplatin, carboplatin, and oxaliplatin), thalidomide and related analogs (e.g., CC-5013 and CC-4047), monoclonal antibodies, and antiangiogenic agents.

As used herein, the term "contacting" means brining a compound of this invention and at least one PK together in a way that the compound can decrease the activity of the at least one PK, either directly, i.e., by acting on the protein kinase itself, or indirectly, i.e., by acting on another molecule on which the activity of the at least one PK is dependent. "Contacting" can occur in vitro or in vivo. For instance, in a test tube that contains the at least one PK; in a culture dish that has whole cells grown; or in a mammal to which the compound of this invention is administered. Examples of target PK include, but are not limited to EGFR, CDK1, Aurora A & B kinase, MAP, CDK2, Raf, NEK (including NEK 4a, NEK 4b, NEK 5 and NEK 6), BUB1, VEGFR, C-MET, HER2, HER3, HER4, IR, IGF-IR, IRR, PDGFRct, PDGFRO, CSFIR, C-Kit, C-fms, Flk-1 R, Flk4, KDRIFIk-1, FLT-1, FLT3, FGFR-1, FGFR-2, FGFR-3, FGFR4, Src, Frk, Btk, Csk, Abl, ZAP70, Fes, Fps, Fak, Jak, Ack, Yes, Fyn, Lyn, Lck, Blk, Hck, Fgr, Aur2, and Yrk.

To practice methods of this invention, the above-described pharmaceutical compositions can be administered orally, parenterally, by inhalation spray, topically, rectally, nasally, buccally, vaginally or via an implanted reservoir. The term "parenteral" as used herein includes subcutaneous, intracutaneous, intravenous, intramuscular, intraarticular, intraarterial, intrasynovial, intrasternal, intrathecal, intralesional, and intracranial injection or infusion techniques. In accordance with some embodiments of the invention, a quinazoline compound of this invention may be administered intravenously, suitable carriers may include but not limited to, physiological saline or phosphate buffered saline (PBS), and solutions containing thickening and solubilizing agents, such as glucose, polyethylene glycol, and polypropylene glycol and mixtures thereof.

A sterile injectable composition, e.g., a sterile injectable aqueous or oleaginous suspension, can be formulated according to techniques known in the art using suitable dispersing or wetting agents (such as Tween 80) and suspending agents. The sterile injectable preparation can also be a sterile injectable solution or suspension in a non-toxic parenterally acceptable diluent or solvent, for example, as a solution in 1,3-butanediol. Among the acceptable vehicles and solvents that can be employed are mannitol, water, Ringer's solution and isotonic sodium chloride solution. In addition, sterile, fixed oils are conventionally employed as a solvent or suspending medium (e.g., synthetic mono- or diglycerides). Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions can also contain a long-chain alcohol diluent or dispersant, or carboxymethyl cellulose or similar dispersing agents. Other commonly used surfactants such as Tweens or Spans or other similar emulsifying agents or bioavailability enhancers which are commonly used in the manufacture of pharmaceutically acceptable solid, liquid, or other dosage forms can also be used for the purposes of formulation.

A composition for oral administration can be any orally acceptable dosage form including, but not limited to, capsules, tablets, emulsions and aqueous suspensions, dispersions and solutions. In the case of tablets for oral use, carriers that are commonly used include lactose and corn starch. Lubricating agents, such as magnesium stearate, are also typically added. For oral administration in a capsule form, useful diluents include lactose and dried corn starch. When aqueous suspensions or emulsions are administered orally, the active ingredients can be suspended or dissolved in an oily phase combined with emulsifying or suspending agents. If desired, certain sweetening, flavoring, or coloring agents can be added. A nasal aerosol or inhalation composition can be prepared according to techniques well known in the art of pharmaceutical formulation. A quinazoline compound-containing composition can also be administered in the form of suppositories for rectal administration.

A carrier in the pharmaceutical composition should be "acceptable" in the sense of being compatible with an active ingredient of the formulation (and preferably, capable of stabilizing it) and not deleterious to the subject to be treated. One or more solubilizing agents (e.g., cyclodextrins) which form more soluble complexes with the active quinazoline compounds can be utilized as pharmaceutical carriers for delivery of the active compounds. Examples of other carriers include colloidal silicon dioxide, magnesium stearate, sodium lauryl sulfate, and D&C Yellow #10.

Compounds of the invention have been shown to be effective inhibitors of PKs and can inhibit cancer cell growth both in vitro and in vivo. Suitable in vitro assays can be used to preliminarily evaluate the efficacy of the quinazoline compounds of this invention in anticancer activities such as inhibiting growth of tumor cells. The compounds can further be examined for their efficacy in treating cancer. For example, a compound can be administered to an animal (e.g., a mouse model) having cancer and its therapeutic effects are then assessed. Based on the results, an appropriate dosage range and administration route can also be determined.

Without further elaboration, it is believed that the above description has adequately enabled the present invention. The following examples are, therefore, to be construed as merely illustrative, and not limitative of the remainder of the disclosure in any way whatsoever. All of the publications cited herein are hereby incorporated by reference in their entirety.

Embodiments of the invention will be further illustrated with the following examples. One of ordinary skill in the art would appreciate that these examples are for illustration only and that various modifications and variations are possible without departing from the scope of the invention. Therefore, these examples are not intended to limit the scope of the invention.

Example 1

Synthesis of 4-(4-(3-hydroxyphenylamino)quinazolin-6-yl)-2-methoxyphenol (8)

The synthesis of 4-(4-(3-hydroxyphenylamino)quinazolin-6-yl)-2-methoxyphenol (8) as an example is depicted in Scheme 2, with referenced to Scheme 1. Briefly, an EtOH solution containing 6-bromo-4-chloro-quinazoline (5.0 g, 21 mmol, 1.0 equiv) and 3-aminophenol (3.36 g, 30.8 mmol, 1.5 equiv) was heated at reflux for 12 h. The solution was cooled to room temperature and the resultant precipitate was collected by filtration, washed with EtOH, and dried in vacuum oven to give compound F (4.90 g, 15.4 mmol) as yellow solids in 73% yield: ESI-MS m/z 316.0 (M+H)$^+$.

Compound F (2.0 g, 6.3 mmol, 1.0 equiv) was mixed with tetrakis(triphenylphosphine)palladium (Pd(PPh$_3$)$_4$, 0.73 g, 0.63 mmol), 2-methoxy-4-(4,4,5,5-tetramethyl-1,3,2dioxaborolan-2-yl)phenol (2.37 g, 9.5 mmol, 1.5 equiv), and Na$_2$CO$_3$ (2.0 equiv) in DMF (80 mL), EtOH (10 mL), and H$_2$O (20 mL). The reaction mixture was heated at reflux for 12 h and filtered through celite. The filtrate was added with water and the resultant solids were collected, washed with CH$_2$Cl$_2$ and MeOH, and dried under vacuum to give 8 (1.90 g, 5.29 mmol) in 84% yield: ESI-MS m/z 360.0 (M+H)$^+$.

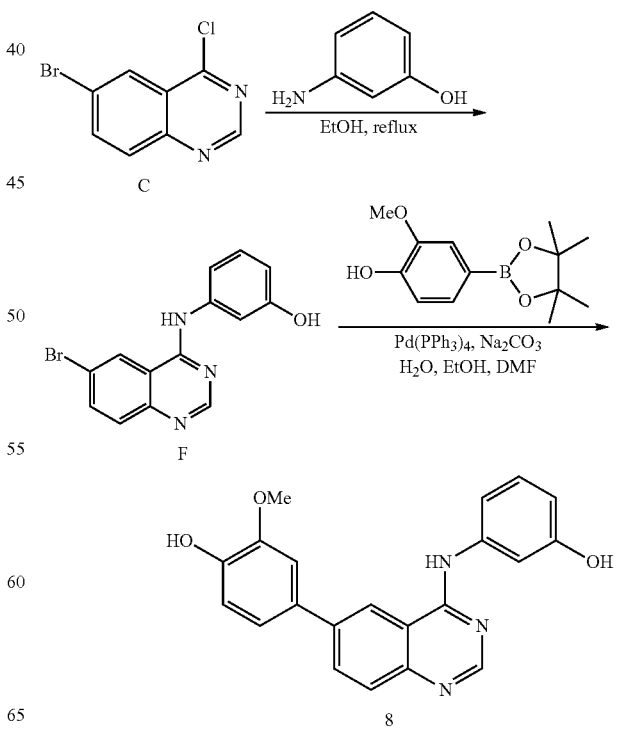

Example 2

Syntheses of Other Compounds Listed in Table 1

Other quinazoline compounds listed in Table 1 above were synthesized in a manner similar to those describe in Example 1. Their calculated mass and observed ESI-MS data are provided in Table 2.

TABLE 2

| Compd ID | Calculated Mass | Observed ESI-MS |
|---|---|---|
| 1 | 343.13 | 344.0 (M + H)+ |
| 2 | 345.13 | 346.0 (M + H)+ |
| 3 | 327.14 | 328.0 (M + H)+ |
| 4 | 313.12 | 314.0 (M + H)+ |
| 5 | 312.14 | 313.0 (M + H)+ |
| 6 | 431.17 | 432.0 (M + H)+ |
| 7 | 462.17 | 344.0 (M − C$_6$H$_5$NHCO + H)+ |
| 8 | 359.13 | 360.0 (M + H)+ |
| 9 | 414.17 | 415.0 (M + H)+ |
| 10 | 327.14 | 328.0 (M + H)+ |
| 11 | 355.14 | 356.0 (M + H)+ |
| 12 | 383.17 | 384.0 (M + H)+ |
| 13 | 403.15 | 404.0 (M + H)+ |
| 14 | 395.08 | 396.0 (M + H)+ |
| 15 | 361.12 | 362.0 (M + H)+ |
| 16 | 395.08 | 396.0 (M + H)+ |
| 17 | 375.14 | 376.0 (M + H)+ |
| 18 | 411.12 | 412.0 (M + H)+ |
| 19 | 359.13 | 360.0 (M + H)+ |
| 20 | 379.11 | 380.0 (M + H)+ |
| 21 | 393.09 | 394.0 (M + H)+ |
| 22 | 373.14 | 374.0 (M + H)+ |
| 23 | 359.13 | 360.0 (M + H)+ |
| 24 | 404.13 | 405.0 (M + H)+ |
| 25 | 389.14 | 390.2 (M + H)+ |
| 26 | 511.13 | 513.0 (M + H)+ |
| 27 | 422.10 | 423.0 (M + H)+ |
| 28 | 452.13 | 453.0 (M + H)+ |
| 29 | 373.14 | 374.0 (M + H)+ |
| 30 | 373.14 | 374.0 (M + H)+ |
| 31 | 389.14 | 390.0 (M + H)+ |
| 32 | 387.12 | 388.0 (M + H)+ |
| 33 | 386.14 | 370.0 (M + H − 16)+ |
| 34 | 403.12 | 404.0 (M + H)+ |
| 35 | 386.14 | 387.0 (M + H)+ |
| 36 | 388.12 | 389.0 (M + H)+ |
| 37 | 358.14 | 359.0 (M + H)+ |
| 38 | 387.12 | 388.0 (M + H)+ |
| 39 | 383.14 | 384.0 (M + H)+ |
| 40 | 382.14 | 383.0 (M + H)+ |
| 41 | 403.15 | 404.0 (M + H)+ |
| 42 | 419.15 | 420.0 (M + H)+ |
| 43 | 423.10 | 424.0 (M + H)+ |
| 44 | 400.15 | 401.0 (M + H)+ |
| 45 | 454.13 | 359.0 (M − COCF$_3$ + H)+ |
| 46 | 422.10 | 423.0 (M + H)+ |
| 47 | 386.14 | 387.0 (M + H)+ |
| 48 | 417.13 | 418.0 (M + H)+ |
| 49 | 359.13 | 360.0 (M + H)+ |
| 50 | 387.12 | 386.0 (M − H)− |
| 51 | 383.14 | 384.0 (M + H)+ |
| 52 | 361.12 | 362.0 (M + H)+ |
| 53 | 373.14 | 374.0 (M + H)+ |
| 54 | 383.14 | 384.0 (M + H)+ |
| 55 | 389.14 | 390.0 (M + H)+ |
| 56 | 436.12 | 435.0 (M − H)− |
| 57 | 387.12 | 386.0 (M − H)− |
| 58 | 377.12 | 378.0 (M + H)+ |
| 59 | 393.09 | 394.0 (M + H)+ |
| 60 | 393.09 | 394.0 (M + H)+ |
| 61 | 427.05 | 428.0 (M + H)+ |
| 62 | 329.12 | 330.0 (M + H)+ |
| 63 | 329.12 | 330.0 (M + H)+ |
| 64 | 343.13 | 344.0 (M + H)+ |
| 65 | 490.09 | 491.0 (M + H)+ |
| 66 | 384.13 | 385.0 (M + H)+ |
| 67 | 343.13 | 344.0 (M + H)+ |
| 68 | 358.14 | 357.0 (M − H)− |
| 69 | 352.14 | 353.0 (M + H)+ |
| 70 | 470.12 | 471.0 (M + H)+ |
| 71 | 394.15 | 395.0 (M + H)+ |
| 72 | 406.11 | 407.0 (M + H)+ |
| 73 | 430.12 | 429.0 (M − H)− |
| 74 | 385.13 | 386.0 (M + H)+ |
| 75 | 385.13 | 386.0 (M + H)+ |
| 76 | 401.10 | 402.0 (M + H)+ |
| 77 | 381.16 | 382.0 (M + H)+ |
| 78 | 381.16 | 369.0 (M + H)+ |
| 79 | 389.08 | 390.0 (M + H)+ |
| 80 | 371.09 | 372.0 (M + H)+ |
| 81 | 355.12 | 356.0 (M + H)+ |
| 82 | 384.13 | 385.0 (M + H)+ |
| 83 | 382.14 | 383.0 (M + H)+ |
| 84 | 385.13 | 386.0 (M + H)+ |
| 85 | 373.11 | 374.0 (M + H)+ |
| 86 | 337.13 | 337.9 (M + H)+ |
| 87 | 405.12 | 406.0 (M + H)+ |
| 88 | 362.13 | 362.9 (M + H)+ |
| 89 | 397.15 | 398.0 (M + H)+ |
| 90 | 380.17 | 381.0 (M + H)+ |
| 91 | 355.12 | 355.9 (M + H)+ |
| 92 | 382.12 | 383.0 (M + H)+ |
| 93 | 381.16 | 382.3 (M + H)+ |
| 94 | 367.14 | 368.2 (M + H)+ |
| 95 | 430.12 | 430.5 (M + H)+ |
| 96 | 381.12 | 382.1 (M + H)+ |
| 97 | 380.14 | 378.6 (M − H)− |
| 98 | 395.14 | 395.9 (M + H)+ |
| 99 | 397.15 | 397.5 (M + H)+ |
| 100 | 358.13 | 358.8 (M + H)+ |
| 101 | 376.12 | 377.1 (M + H)+ |
| 102 | 362.13 | 362.7 (M + H)+ |
| 103 | 382.14 | 383.1 (M + H)+ |
| 104 | 369.14 | 369.4 (M + H)+ |
| 105 | 397.15 | 397.5 (M + H)+ |
| 106 | 356.16 | 356.9 (M + H)+ |
| 107 | 416.11 | 416.9 (M + H)+ |
| 108 | 444.14 | 445.0 (M + H)+ |
| 109 | 458.15 | 458.3 (M + H)+ |
| 110 | 415.11 | 416.2 (M + H)+ |
| 111 | 384.14 | 384.9 (M + H)+ |
| 112 | 384.14 | 384.8 (M + H)+ |
| 113 | 396.16 | 396.6 (M + H)+ |
| 114 | 361.13 | 362.1 (M + H)+ |
| 115 | 400.11 | 400.7 (M + H)+ |
| 116 | 394.14 | 395.2 (M + H)+ |
| 117 | 379.14 | 378.2 (M − H)− |
| 118 | 409.12 | 410.0 (M + H)+ |
| 119 | 361.12 | 362.0 (M + H)+ |
| 120 | 414.12 | 415.1 (M + H)+ |
| 121 | 351.15 | 351.7 (M + H)+ |
| 122 | 457.16 | 458.1 (M + H)+ |
| 123 | 366.15 | 367.0 (M + H)+ |
| 124 | 352.13 | 352.9 (M + H)+ |
| 125 | 354.13 | 355.2 (M + H)+ |
| 126 | 417.10 | 417.9 (M + H)+ |
| 127 | 399.13 | 399.8 (M + H)+ |
| 128 | 453.12 | 453.8 (M + H)+ |
| 129 | 454.11 | 454.8 (M + H)+ |
| 130 | 454.11 | 454.5 (M + H)+ |
| 131 | 353.13 | 354.3 (M + H)+ |
| 132 | 297.13 | 298.2 (M + H)+ |
| 133 | 313.12 | 314.2 (M + H)+ |
| 134 | 379.11 | 380.1 (M + H)+ |
| 135 | 407.14 | 408.4 (M + H)+ |
| 136 | 401.13 | 401.7 (M + H)+ |
| 137 | 369.14 | 370.0 (M + H)+ |
| 138 | 370.13 | 370.7 (M + H)+ |
| 139 | 470.08 | 471.0 (M + H)+ |
| 140 | 470.08 | 470.7 (M + H)+ |
| 141 | 469.09 | 469.8 (M + H)+ |
| 142 | 389.08 | 389.8 (M + H)+ |
| 143 | 353.13 | 354.2 (M + H)+ |

TABLE 2-continued

| Compd ID | Calculated Mass | Observed ESI-MS |
|---|---|---|
| 144 | 367.14 | 367.7 (M + H)+ |
| 145 | 453.12 | 453.7 (M + H)+ |
| 146 | 366.15 | 367.1 (M + H)+ |
| 147 | 367.14 | 367.7 (M + H)+ |
| 148 | 352.13 | 353.1 (M + H)+ |
| 149 | 401.13 | 401.9 (M + H)+ |
| 150 | 472.10 | 472.9 (M + H)+ |
| 151 | 351.14 | 351.8 (M + H)+ |
| 152 | 344.12 | 344.9 (M + H)+ |
| 153 | 377.14 | 377.6 (M + H)+ |
| 154 | 373.14 | 373.7 (M + H)+ |
| 155 | 397.15 | 398.1 (M + H)+ |
| 156 | 391.13 | 391.6 (M + H)+ |
| 157 | 393.09 | 393.8 (M + H)+ |
| 158 | 395.11 | 395.7 (M + H)+ |
| 159 | 411.08 | 412.0 (M + H)+ |
| 160 | 383.06 | 383.6 (M + H)+ |
| 161 | 377.12 | 377.8 (M + H)+ |
| 162 | 395.11 | 396.2 (M + H)+ |
| 163 | 389.11 | 390.1 (M + H)+ |
| 164 | 383.06 | 384.0 (M + H)+ |

Example 3

Biological Activity

Various compounds of formula (I) and (II) were tested for their abilities to inhibit a variety of protein kinases, such as B-Raf, B-Raf (V600E), C-Raf, EGFR, EGFR (T790M), VEGFR-2, FGFR1 and CDK1 kinases. Brief descriptions of different assays are described as follows.

A. Raf Kinase Assays (B-Raf, B-raf (V600E), and C-Raf)

Inhibition of kinase activity by test compound disclosed herein was estimated by quantifying the amount of [$^{33}$P] incorporation of substrate in the presence of test compound. Standard assay conditions were 2 ng of recombinant C-Raf or 5 ng of recombinant B-Raf or 5 ng of recombinant B-Raf (V600E) kinase (Upstate Biotechnology) with 500 ng MEK1 (K97R) in assay buffer {8 μM ATP, 0.5 μCi [$^{33}$P]ATP (specific activity 3000 Ci/mmol, PerkinElmer), 50 mM Tris/HCl (pH7.5), and 1 mM EGTA, 1 mM Na$_3$VO$_4$, 1% 2-mercaptoethanol, 0.1% Brij 35, and 0.2 mg/ml BSA} at a final volume of 25 μL. Reactions were incubated at 30° C. for 30 min and stopped by adding 3% phosphoric acid, harvested onto a 96-well GF/B UniFilter (PerkinElmer) using a unifilter harvester (PerkinElmer), and counted with a TopCount microplate scintillation counter (PerkinElmer). The IC$_{50}$ values of inhibitors were determined after carrying out assays at 3-fold serially diluted concentrations of each compound in duplication. The results were analyzed using linear regression software (GraphPad Prism 4; GraphPad Software Inc.). Inhibition of B-Raf, B-raf (V600E), and C-Raf kinases by various compounds listed in Table 1 are summarized and shown in Table 3 below. IC$_{50}$ value is defined as the concentration of the test compound which achieves a half-maximal inhibition of the kinase activity.

TABLE 3

| | B-Raf inhibition at | IC$_{50}$ (nM) | | |
|---|---|---|---|---|
| Compd ID | 1.0 μM | B-Raf | B-Raf (V600E) | C-Raf |
| 1 | — | 900 | 760 | 2,150 |
| 2 | — | — | — | — |
| 3 | — | 3292 | 3394 | >10,000 |
| 4 | — | 3986 | 4870 | 9456 |
| 5 | — | — | — | — |
| 6 | — | — | — | — |
| 7 | 23.5% | — | — | — |
| 8 | 94.2% | 30.2 | 37.4 | 255 |
| 9 | 13.8% | — | — | — |
| 10 | 15.8% | — | — | — |
| 11 | 19.9% | — | — | — |
| 12 | 18.2% | — | — | — |
| 13 | 7.7% | — | — | — |
| 14 | 52.7% | 1,014 | 1,088 | 2,157 |
| 15 | 44.4% | 1,154 | 1,024 | 1,452 |
| 16 | 51.5% | 817.2 | 809.6 | 1,249 |
| 17 | 59.4% | 647.1 | 618.6 | 1,906 |
| 18 | 48.9% | 3,136 | 1,169 | >10,000 |
| 19 | 55.8% | 557 | 522 | 503.2 |
| 20 | 55.3% | 593.7 | 470.9 | 882.1 |
| 21 | 47.6% | 1,125 | 1,357 | 809.9 |
| 22 | 63.3% | 719 | 411 | 1,386 |
| 23 | 62.6% | 669 | 377 | 3,094 |
| 24 | 48.6% | 1,695 | 1,807 | — |
| 25 | 54.9% | 1,106 | 842 | 1,557 |
| 26 | 45.7% | — | — | — |
| 27 | 77.2% | 415 | 453 | 887 |
| 28 | 30.5% | — | — | — |
| 29 | 85.7% | 177 | 212 | 1,062 |
| 30 | 10.0% | — | — | — |
| 31 | 93.8% | 87 | 94 | 781 |
| 32 | 34.7% | — | — | — |
| 33 | 53.6% | 666.8 | 2,344 | >3,000 |
| 34 | 65.0% | 494.2 | 571.5 | 579.8 |
| 35 | 74.9% | 317.4 | 290.5 | 970.4 |
| 36 | 76.3% | 255.7 | 674.8 | 6,993 |
| 37 | 65.8% | 572.8 | 848.6 | 1,307 |
| 38 | 57.5% | 659.5 | 706.7 | 1,400 |
| 39 | 51.6% | 1,030 | 1,440 | 3,278 |
| 40 | 32.2% | — | — | — |
| 41 | 82.2% | 266.5 | 348.6 | >10,000 |
| 42 | 20.4% | — | — | — |
| 43 | 94.3% | 40.4 | 47.3 | 245.4 |
| 44 | 65.3% | 489 | 382 | 685.1 |
| 45 | 73.9% | 381.6 | 358 | 835.4 |
| 46 | 64.4% | 623.7 | 576.5 | 1,963 |
| 47 | 37.8% | — | — | — |
| 48 | 30.6% | — | — | — |
| 49 | 90.3% | 55.3 | 71.6 | 789.8 |
| 50 | 15.6% | — | — | — |
| 51 | 86.0% | 121.3 | 157.4 | 404.4 |
| 52 | 69.2% | 560.1 | 544.1 | 1,304 |
| 53 | 85.5% | 141.4 | 181.4 | 500 |
| 54 | 56.2% | 735.2 | 633.3 | 2,574 |
| 55 | 38.1% | — | — | — |
| 56 | 64.1% | 462.6 | 430.1 | 1,410 |
| 57 | 4.8% | — | — | — |
| 58 | 92.6% | 16.1 | 23.2 | 169.5 |
| 59 | 92.6% | 36.5 | 64.7 | 290.4 |
| 60 | 91.0% | 39 | 56.5 | 151.8 |
| 61 | 92.6% | 40.1 | 59.9 | 284.1 |
| 62 | 93.8% | 32.5 | 60.1 | 334.6 |
| 63 | 93.4% | 27.7 | 51.7 | 299.5 |
| 64 | 91.9% | 62.4 | 104.6 | 1,227 |
| 65 | 40.4% | — | — | — |
| 66 | 59.3% | 1,011 | 932.8 | 973.1 |
| 67 | 84.3% | 102.6 | 139.2 | 2,398 |
| 68 | 83.7% | 55.8 | 76.6 | 860.3 |
| 69 | 75.0% | 259.8 | 341.7 | 957 |
| 70 | −6.5 | — | — | — |
| 71 | 77.2% | 373 | 392.7 | 935 |
| 72 | 93.4% | 73.8 | 90 | 860.9 |
| 73 | 72.5% | 366.1 | 486.7 | 1,426 |
| 74 | 91.2% | 113.8 | 139.3 | 750.9 |
| 75 | 85.0% | 156.9 | 220.8 | 672.4 |

TABLE 3-continued

| Compd ID | B-Raf inhibition at 1.0 μM | IC$_{50}$ (nM) B-Raf | B-Raf (V600E) | C-Raf |
|---|---|---|---|---|
| 76 | 86.1% | 215.7 | 240.1 | 875.6 |
| 77 | 61.7% | 697.7 | 911.3 | 2,534 |
| 78 | 71.1% | 470.4 | 735.8 | 1,856 |
| 79 | 69.6% | 513.6 | 556.9 | 1,221 |
| 80 | 77.2% | 286.8 | 289 | 918.7 |
| 81 | 79.1% | 244 | 279.5 | 587.5 |
| 82 | 58.0% | 668.2 | 702.2 | 1,274 |
| 83 | 36.3% | — | — | — |
| 84 | 83.1% | 171.8 | 194.8 | 756.9 |
| 85 | 83.0% | 173.9 | 209.3 | 494.6 |
| 86 | 77.8% | 201.1 | 287.3 | 597 |
| 87 | 71.3% | 356.1 | 370.8 | 843.6 |
| 88 | 77.4% | 248.9 | 299.2 | 630.3 |
| 89 | 80.4% | 205 | 258.7 | 868.7 |
| 90 | 56.1% | 762.5 | 1,007 | 4,080 |
| 91 | 85.3% | 154.9 | 255.3 | 708.8 |
| 92 | 66.3% | 428.3 | 535.1 | 1,610 |
| 93 | 76.6% | 346.8 | 355.1 | 1,560 |
| 94 | 76.2% | 430 | 551.3 | 1,408 |
| 95 | 70.9% | 430 | 534.2 | 1286 |
| 96 | 86.1% | 141.1 | 161 | 568.3 |
| 97 | 86.6% | 112 | 150.6 | 584.2 |
| 98 | 92.5% | 73.9 | 104.8 | 337.9 |
| 99 | 61.1% | 357.9 | 450.7 | 3,914 |
| 100 | 95.8% | 21 | 23 | 135.9 |
| 101 | 97.1% | 18.1 | 20.9 | 96.1 |
| 102 | 87.0% | 134 | 199.2 | 293.7 |
| 103 | 85.2% | 164.1 | 211.4 | 354.1 |
| 104 | 81.1% | 235.1 | 356.6 | 777.5 |
| 105 | 72.6% | 379.9 | 515 | 2134 |
| 106 | 78.7% | 272.1 | 292.3 | 3,192 |
| 107 | 75.4% | 344.8 | 327.6 | 677.1 |
| 108 | 81.1% | 221.3 | 243.6 | 679.6 |
| 109 | 85.1% | 125.8 | 164.1 | 520.9 |
| 110 | 81.8% | 247.6 | 272.6 | 650.4 |
| 111 | 89.1% | 83.4 | 99.9 | 290.4 |
| 112 | 80.2% | 181.9 | 206.9 | 619.3 |
| 113 | 75.5% | 262.7 | 291 | 971.7 |
| 114 | 82.3% | 99.2 | 122.8 | 287.4 |
| 115 | 76.6% | 266.8 | 278.4 | 734.7 |
| 116 | 88.4% | 99.6 | 116.8 | 233.2 |
| 117 | 86.6% | 107.2 | 113.6 | 321 |
| 118 | 68.2% | 548.2 | 525.4 | 988.1 |
| 119 | 67.1% | 543.2 | 632.9 | 1,442 |
| 120 | 88.2% | 134.3 | 118.6 | 276.7 |
| 121 | 76.2% | 227.1 | 284.5 | 753.2 |
| 122 | 77.5% | 258.6 | 263.8 | 439.4 |
| 123 | 80.3% | 231.1 | 263.4 | 688.5 |
| 124 | 82.4% | 187.9 | 185.2 | 409.3 |
| 125 | 71.2% | 285.1 | 422.7 | 1,030 |
| 126 | 83.6% | 141.7 | 162.1 | 286.9 |
| 127 | 53.5% | 887.6 | 1087 | 8,394 |
| 128 | 18.5% | 4,134 | 4,284 | 12,840 |
| 129 | 77.5% | 240.3 | 270.3 | 1,059 |
| 130 | 44.1% | — | — | — |
| 131 | 80.1% | 451.1 | 547.3 | 4213 |
| 132 | 22.4% | — | — | — |
| 133 | 85.8% | 168 | 253.5 | 6637 |
| 134 | 57.7% | 759.7 | 706.5 | 4,421 |
| 135 | 24.0% | — | — | — |
| 136 | 84.9% | 349.5 | 268.1 | 1,127 |
| 137 | 78.2% | 148.7 | 152.3 | 1,326 |
| 138 | 72.5% | 250.8 | 253.3 | 2,367 |
| 139 | 25.8% | — | — | — |
| 140 | 24.3% | — | — | — |
| 141 | 4.6% | — | — | — |
| 142 | 23.3% | — | — | — |
| 143 | 75.4% | 227.1 | 357 | 1,963 |
| 144 | 62.6% | 308.9 | 471.7 | 3,901 |
| 145 | 7.5% | — | — | — |
| 146 | 64.3% | 614.2 | 426 | 3696.2 |
| 147 | 50.7% | 679.7 | 848.3 | 2948.5 |
| 148 | 68.9% | 229.9 | 359.2 | 583.7 |
| 149 | 15.2% | — | — | — |
| 150 | 37.2% | — | — | — |
| 151 | −5.4% | — | — | — |
| 152 | 86.4% | 131.4 | 197.7 | 2,331 |
| 153 | 84.4% | 188.1 | 236.2 | 722.9 |
| 154 | 88.4% | 60.0 | 70.9 | 590.5 |
| 155 | 8.2% | — | — | — |
| 156 | 92.4% | 57.3 | 81.7 | 301.1 |
| 157 | 92.0% | 26.8 | 37.5 | 160.6 |
| 158 | 96.4% | 3.8 | 7.1 | 36.3 |
| 159 | 97.4% | 11.1 | 19.7 | 69.2 |
| 160 | 97.9% | 8.9 | 19 | 146.7 |
| 161 | 94.7% | 16.9 | 23.4 | 132.8 |
| 162 | 94.6% | 2.9 | 4.5 | 197.4 |
| 163 | 94.2% | 2.4 | 4.5 | 256 |
| 164 | 83.0% | 151 | 216.5 | 3,512 |

B. EGFR Kinase Assay

Inhibition of EGFR kinase activity by compounds disclosed herein is quantified by measuring the amount of [$^{33P}$] incorporated into the substrate in the presence of a test compound. Briefly, a reaction mixture of 25 μL final volume containing 25 ng of EGFR kinase (EGFR kinase domain alone, Millipore), 3 μg of the substrate [poly(Glu-Tyr), Sigma], kinase reaction buffer (10 mM MOPS pH 7.0, 0.3 mM EDTA, 0.5% glycerol, 0.001% Brij-35, 10 mM MnCl$_2$, 0.1 mg/ml BSA, 100 μM ATP, 0.1 μCi per well [$^{33P}$]-γ-ATP (2,500-3,000 Ci/mmol)), and a test compound (100 nM, diluted with 4% DMSO) or DMSO (as the control) was incubated at 30° C. for 30 minutes. The reaction was stopped by adding 5 μL of 3% phosphoric acid solution. The resultant reaction solution was then harvested onto a filter plate (Uni-Filter-96 GF/B, PerkinElmer), washed 20 times for 5 min with d.d. H$_2$O, and followed by the addition of 30 μL of MicroScint™-20 Cocktail (PerkinElmer). The radioactivity retained on the filter membrane was measured by Top-Count™ scintillation detector (PerkinElmer). The results were analyzed by using linear regression software (GraphPad Prism™ 4; GraphPad Software Inc.). Results of inhibition of EGFR kinase by representative compounds listed in Table 1 are shown in Table 4 below. IC$_{50}$ value is defined as the concentration of the test compound which achieves a half-maximal inhibition of the kinase activity.

C. EGFR (T790M) Kinase Assay

Inhibition of EGFR (T790M) kinase activity by compounds disclosed herein was quantified by measuring the amount of [$^{33P}$] incorporated into the substrate in the presence of a test compound. Briefly, a reaction mixture of 25 μL final volume containing 25 ng of EGFR (T790M) kinase (EGFR (T790M) kinase domain alone, Millipore), 5 μg of the substrate [poly(Glu-Tyr), Sigma], kinase reaction buffer (10 mM MOPS pH 7.0, 0.3 mM EDTA, 0.5% glycerol, 0.001% Brij-35, 10 mM MnCl$_2$, 0.1 mg/ml BSA, 100 μM ATP, 0.1 μCi per well [$^{33P}$]-γ-ATP (2,500-3,000 Ci/mmol)), and a test compound (100 nM; diluted with 4% DMSO) or DMSO (as the control) was incubated at 30° C. for 60 minutes. The reaction was stopped by adding 5 μL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The radioactivity retained on the filter membrane was measured by Top-Count™ scintillation detector (PerkinElmer). The results were analyzed by using linear regression software (GraphPad Prism™ 4; GraphPad Software Inc.). The percentage of inhibition of EGFR (T790M) by the test compound was calculated by dividing the retained radioactivity of the test sample with the retained radioactivity of the control sample and shown in Table 4.

D. VEGFR2 Kinase Assay

Inhibition of VEGFR2 kinase activity by compounds disclosed herein was quantified by measuring the amount of [$^{33P}$] incorporated into the substrate in the presence of a test compound. Specifically, a reaction mixture with a final volume of 25 μL and containing 6.25 ng of VEGFR2 kinase (obtained by purifying recombinant N-terminal 6×His-tagged VEGFR2 kinase domain construct expressed by baculovirus), 5 μg of substrate (Poly(Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 100 μM ATP, 0.1 μCi per well [$^{33P}$]-γ-ATP (2,500-3,000 Ci/mmol), and 500 nM test compound (final concentration of DMSO was 4%) or 4% DMSO alone (as the control sample), was incubated at 30° C. for 30 minutes. The reaction was then stopped by adding 5 μL of 3% phosphoric acid solution. The resultant solution was transferred to and harvested by a filter plate (UniFilter-96 GF/B, PerkinElmer). The filter plate was then washed 20 times with d.d. H$_2$O for 5 min followed by the addition of 30 μL of MicroScint™-20 Cocktail (PerkinElmer). After the plate was sealed, the retained radioactivity on the filter was counted using a TopCount™ scintillation detector (PerkinElmer). The percentage of inhibition rate of the test compound was calculated by dividing the retained radioactivity of the test sample with the retained radioactivity of the control sample and shown in Table 4.

E. FGFR1 Kinase Assay

Inhibition of FGFR1 kinase activity by compounds disclosed herein was quantified by measuring the amount of [$^{33P}$] incorporated into the substrate in the presence of a test compound. Briefly, a reaction mixture of 25 μL final volume containing 1 ng of FGFR1 kinase (FGFR1 kinase domain alone, Millipore), 5 μg of the substrate [poly(Glu-Tyr), Sigma], kinase reaction buffer (14 mM MOPS pH 7.0, 0.2 mM EDTA, 0.5% glycerol, 0.001% Brij-35, 0.01% β-mercaptoethanol, 0.1 mg/ml BSA, 100 μM ATP, 0.1 μCi per well [$^{33P}$]-γ-ATP (2,500-3,000 Ci/mmol)), and a test compound (100 nM, diluted with 4% DMSO) or DMSO (as the control) was incubated at 30° C. for 60 minutes. The reaction was stopped by adding 5 μL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The radioactivity retained on the filter membrane was measured by TopCount™ scintillation detector (PerkinElmer). The results were analyzed by using linear regression software (GraphPad Prism™ 4; GraphPad Software Inc.). Results of inhibition of FGFR1 kinase by representative compounds listed in Table 1 are shown in Table 4 below. IC$_{50}$ value is defined as the concentration of the test compound which achieves a half-maximal inhibition of the kinase activity.

F. FLT3 Kinase Assay

Inhibition of FLT3 kinase activity by compounds disclosed herein was quantified by measuring the amount of [$^{33P}$] incorporated into the substrate in the presence of a test compound. Briefly, a reaction mixture of 25 μL final volume containing 5 ng of Flt3 kinase (obtained by purifying recombinant N-terminal 6×His-tagged Flt3 kinase domain construct expressed from baculovirus), 5 μg of the substrate (Poly(Glu-Tyr, 4:1, Sigma)), kinase reaction buffer (20 mM MOPS pH 7.0, 1 mM EDTA, 5% glycerol, 0.01% Brij-35, 0.1% β-mercaptoethanol, 1 mg/mL BSA, 100 μM ATP, 0.1 μCi per well [$^{33P}$]-γ-ATP (2,500-3,000 Ci/mmol)), and a test compound (100 nM, diluted with 4% DMSO) or DMSO (as the control) was incubated at 30° C. for 30 minutes. The reaction was stopped by adding 5 μL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The plate was then sealed and counted using a TopCount™ scintillation detector (PerkinElmer). Results of inhibition of FLT3 kinase by representative compounds listed in Table 1 are shown in Table 4 below. IC$_{50}$ value is defined as the concentration of the test compound which achieves a half-maximal inhibition of the kinase activity.

G. CDK1 Kinase Assay

Inhibition of Cdk1 kinase activity by compounds disclosed herein was quantified by measuring the amount of [$^{33P}$] incorporated into the substrate in the presence of a test compound. Briefly, a reaction mixture of 25 μL final volume containing 5 ng of Cdk1 kinase (Cdk1 kinase domain alone, Millipore), 3 μg of the substrate [Histone H1], kinase reaction buffer (10 mM MOPS pH 7.0, 0.3 mM EDTA, 0.5% glycerol, 0.001% Brij-35, 0.1 mg/ml BSA, 10 μM ATP, 0.1 μCi per well [$^{33P}$]-γ-ATP (2,500-3,000 Ci/mmol)), and a test compound (100 nM, diluted with 4% DMSO) or DMSO (as the control) was incubated at 30° C. for 30 minutes. The reaction was stopped by adding 5 μL of 3% phosphoric acid solution. The resultant reaction solution was then harvested onto a filter plate (UniFilter-96 GF/B, PerkinElmer), washed 20 times for 5 min with d.d. H$_2$O, and followed by the addition of 30 μL of MicroScint™-20 Cocktail (PerkinElmer). The radioactivity retained on the filter membrane was measured by TopCount™ scintillation detector (PerkinElmer). The results were analyzed by using linear regression software (GraphPad Prism™ 4; GraphPad Software Inc.). Results of inhibition of CDK1 kinase by representative compounds listed in Table 1 are shown in Table 4 below.

TABLE 4

| Compd ID | IC$_{50}$ (nM) | | | | | |
|---|---|---|---|---|---|---|
| | EGFR | EGFR (T790M) | VEGFR2 | FGFR1 | FLT3 | CDK1 |
| 8 | 18.7 | 66% inhibition at 1.0 1 μM | 139.0 | 413.2 | 271.0 | 88% inhibition at 1.0 1 μM |
| 19 | 56.4 | — | 5401.8 | 1436.6 | 146.3 | — |
| 58 | 14.9 | 60% inhibition at 1.0 1 μM | 23.5 | 130.8 | 137.2 | 78% inhibition at 1.0 1 μM |

Example 4

Antiproliferative Activity

The anti-proliferative activities of the compounds with formula (I) and formula (II) with respect to four human cancer cell lines (A549, A375, MDA-MB-231, and COLO205) were measured using the CellTiter™-96 assay kit (Promega) following the manufacturer's instructions. In brief, the cells were maintained in DMEM containing 10% FCS and incubated at 37° C. in 5% CO$_2$ atmosphere. Cells were plated at a density of 2000 cells/well of a 96-well plate for 24 h, then treated with different concentrations of the compounds, and incubated for another 72 hours. At the end of the incubation, CellTiter™-96 Aqueous One Solution Reagent (Promega) was added and incubated for another 4.0 hours. Cell viability was determined by measuring absorbance at 490 nm using EMax® microplate reader (Molecular Devices). Data were processed and analyzed using GraphPad Prism version 4. The anti-proliferative activities are summarized in Table 5.

TABLE 5

| compd ID | Anti-proliferative $IC_{50}$ (µM) | | | |
|---|---|---|---|---|
| | A549 | A375 | MDA-MB-231 | COLO205 |
| 1 | 1.3 ± 0.3 | 2.3 ± 0.1 | 1.8 ± 0.2 | 8.5 ± 2.3 |
| 8 | 1.1 ± 0.1 | 0.9 ± 0.2 | 1.5 ± 0.1 | 6.7 ± 0.1 |
| 14 | >50 | >50 | >50 | 31.6 ± 2.5 |
| 15 | 2.5 ± 0.6 | 2.7 ± 0.2 | 4.1 ± 0.3 | 11.8 ± 4.6 |
| 31 | >50 | >50 | >50 | >50 |
| 43 | 2.2 ± 0.4 | 8.7 ± 2.7 | >50 | 24.7 ± 2.4 |
| 49 | >50 | >50 | >50 | >50 |
| 51 | 1.6 ± 0.3 | 1.4 ± 0.1 | 1.6 ± 0.4 | 7.7 ± 0.3 |
| 58 | 0.5 ± 0.2 | 0.5 ± 0.1 | 0.8 ± 0.3 | 3.2 ± 0.3 |
| 59 | 0.6 ± 0.3 | 0.7 ± 0.1 | 0.9 ± 0.2 | 4.5 ± 0.6 |
| 60 | 1.3 ± 0.2 | 1.3 ± 0.3 | 1.7 ± 0.5 | 6.8 ± 0.16 |
| 61 | 1.6 ± 0.4 | 1.9 ± 0.5 | 2.9 ± 0.4 | 7.4 ± 1.9 |
| 62 | 3.7 ± 1.6 | 2.6 ± 0.1 | 7.2 ± 1.4 | 11.7 ± 2.5 |
| 63 | 5.3 ± 1.0 | 2.3 ± 0.6 | 9.5 ± 1.3 | 7.1 ± 1.3 |
| 64 | 11.0 ± 3.3 | 6.0 ± 0.3 | 15.6 ± 0.8 | 17.3 ± 1.9 |
| 68 | 7.0 ± 2.4 | 4.9 ± 1.7 | 11.5 ± 3.8 | 15.7 ± 4.1 |
| 74 | >50 | >50 | >50 | >50 |
| 75 | 9.6 ± 1.2 | 11.1 ± 0.8 | 11.6 ± 1.7 | 18.5 ± 1.1 |
| 84 | 8.9 ± 1.3 | 11.5 ± 1.9 | 14.8 ± 0.5 | 11.5 ± 1.3 |
| 85 | 14.2 ± 0.8 | 11.4 ± 3.0 | 23.2 ± 2.0 | 15.9 ± 4.1 |
| 96 | 14.2 ± 2.4 | 7.7 ± 0.4 | 12.6 ± 1.8 | 13.0 ± 2.4 |
| 97 | >50 | 24.5 ± 7.1 | 12.7 ± 2.0 | 12.7 ± 2.1 |
| 98 | 12.7 ± 5.3 | 7.2 ± 0.6 | 9.6 ± 1.6 | 9.6 ± 1.6 |
| 100 | 1.78 ± 0.2 | 1.4 ± 0.4 | 5.5 ± 0.5 | 5.2 ± 0.2 |
| 101 | 6.7 ± 0.1 | 2.3 ± 0.3 | 21.1 ± 3.8 | 21.1 ± 3.8 |
| 102 | >50 | >50 | >50 | >50 |
| 103 | 3.2 | 6.6 | 4 ± 0.2 | 8.9 |
| 109 | 16.9 ± 0.6 | 14.2 ± 1.0 | 10.1 ± 1.1 | 13.6 ± 1.5 |
| 111 | 25.1 ± 7.1 | 36.3 ± 1.7 | 26.5 ± 7.3 | 32.3 ± 8.5 |
| 114 | 4.8 ± 1.6 | 6.3 ± 0.7 | 6.2 ± 0.6 | 2.6 ± 0.4 |
| 116 | 6.4 ± 0.7 | 5.4 ± 0.7 | 6.2 ± 0.4 | 6.3 ± 0.2 |
| 117 | 23.5 ± 0.5 | 23.7 ± 2.4 | 13.6 ± 0.9 | 8.9 ± 0.1 |
| 120 | 12.1 ± 3.2 | 8.5 ± 1.2 | 10.9 ± 1.4 | 7.3 ± 1.0 |
| 124 | 6.1 ± 0.6 | 7.3 ± 0.6 | 8.5 ± 1.4 | 9.6 ± 0.6 |
| 126 | 2.7 ± 1.7 | 2.9 ± 1.6 | 2.4 ± 1.1 | 16.8 ± 9.3 |
| 133 | 9.3 ± 1.3 | 6.0 ± 1.0 | 33.8 ± 6.9 | 11.5 ± 0.8 |
| 137 | 10.8 ± 0.7 | 23.6 ± 1.2 | 19.5 ± 2.1 | 8.3 ± 0.4 |
| 152 | >50 | >50 | >50 | — |
| 153 | 7.7 ± 0.6 | 6.4 ± 0.9 | 7.8 ± 0.3 | — |
| 154 | 0.9 ± 0.5 | 1 ± 0.2 | 1.0 ± 0.1 | 6.4 ± 0.6 |
| 156 | 1.6 ± 0.4 | 1.9 ± 0.3 | 2.8 ± 0.2 | 9.6 ± 3.8 |
| 157 | 2.5 ± 0.8 | 2.9 ± 0.6 | 4.7 ± 0.3 | 7.8 |
| 158 | 0.9 ± 0.4 | 0.4 ± 0.1 | 1.2 ± 0.1 | 5.1 ± 1.0 |
| 159 | 2.9 ± 0.4 | 2.3 ± 0.5 | 4.3 ± 0.6 | 7.9 ± 1.9 |
| 160 | >30 | 8.2 ± 1.3 | >30 | 20.9 ± 12.6 |
| 161 | 1.5 ± 0.3 | 1.0 ± 0.1 | 2.1 ± 0.5 | 5.2 ± 1.8 |
| 162 | 2.4 ± 0.7 | 1.5 ± 0.1 | 2.1 ± 0.1 | 5.1 ± 1.4 |
| 163 | 26.0 ± 3.2 | 4.1 ± 0.7 | 17.8 ± 0.2 | 15.7 ± 2.0 |

Example 4

In Vivo Anti-Cancer Activities

A375 (1×10⁶ cell/mouse) tumor cells were subcutaneously injected into the right flank of 5 week old male NOD/SCID mice (BioLASCO, Taiwan). Tumor volume was measured with a digital caliper once tumor was palpable (within 10 to 15 days after implantation). Compound treatment was started after 1-3 weeks when the tumors had reached an average volume of ~50 to 100 mm³. Mice were divided into 5 groups as listed in Table 6 below and were given intraperitoneal injections with the test compound at 50 mg/kg, or vehicle control (DMSO:Cremophor:PBS (pH 7.4)=5:10:8.5) one time every day. The test compound, 58, was formulated in a solution of 5% DMSO, 10% Cremophor, and 85% PBS. The positive control, PLX4032, was dissolved in 100% PBS. Body weights of the mice were measured every two to three days and the tumor sizes in different groups of mice were measured by digital caliper every two to three days. Results indicated that compound 58 inhibited tumor growth in vivo without inducing significant weight loss.

TABLE 6

| group | mouse (n) | schedule | administration route |
|---|---|---|---|
| Vehicle control | 5 | qd x 28 | i.p. |
| 58 (50 mg/kg) | 5 | qd x 28 | i.p. |
| PLC4032 (20 mg/kg) | 5 | qd x 28 | p.o. |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. A compound having a structure represented by formula (II)

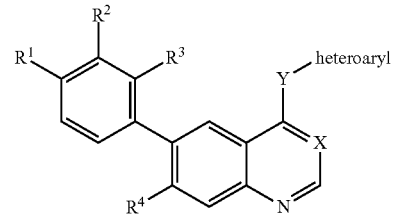

formula (II)

wherein X is N; Y is NH;

wherein the heteroaryl attached to Y is selected from:

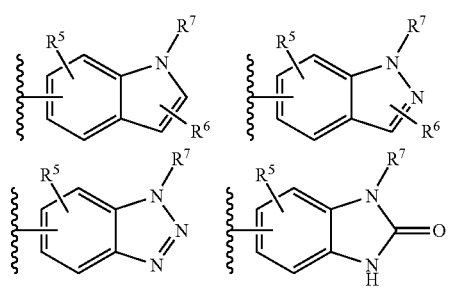

-continued

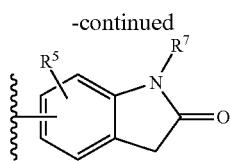

wherein each of $R^5$, $R^6$, and $R^7$, independently, is H, halo, nitro, cyano, aryl, heteroaryl, alkyl, alkenyl, alkynyl, cycloalkyl, heterocycloalkyl, cycloalkenyl, heterocycloalkenyl, —$OR^a$, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —N=$CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl;

one of $R^1$ and $R^2$ is —OH or —$OR^a$ and the other of $R^1$ and $R^2$ is —H, OH, or —$OR^a$, $R^3$, and $R^4$ are independently H or —$OR^a$, wherein $R^a$ is alkyl.

2. A compound having a structure represented by formula (II)

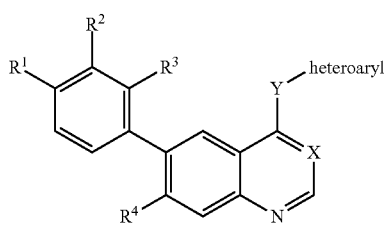

wherein X is CH; Y is NH;
wherein the heteroaryl attached to Y is selected from:

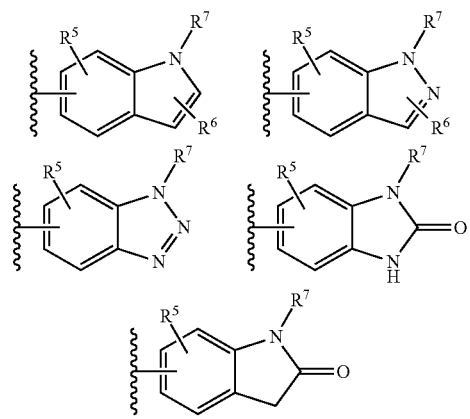

wherein each of $R^5$, $R^6$, and $R^7$, independently, is H, halo, nitro, cyano, aryl, heteroaryl, alkyl, alkenyl, alkynyl, cycloalkyl, heterocycloalkyl, cycloalkenyl, heterocycloalkenyl, —$OR^a$, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —N=$CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl, heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl;

one of $R^1$ and $R^2$ is —OH or —$OR^a$ and the other of $R^1$ and $R^2$ is —H, OH, or —$OR^a$, $R^3$, and $R^4$ are independently H or —$OR^a$, wherein $R^a$ is alkyl.

3. A compound of Formula (A),

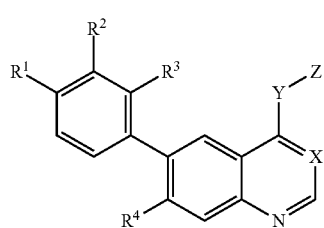

wherein X is N; Y is NH:
Z is

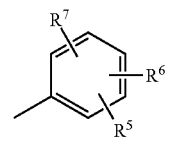

or a heteroaryl selected from

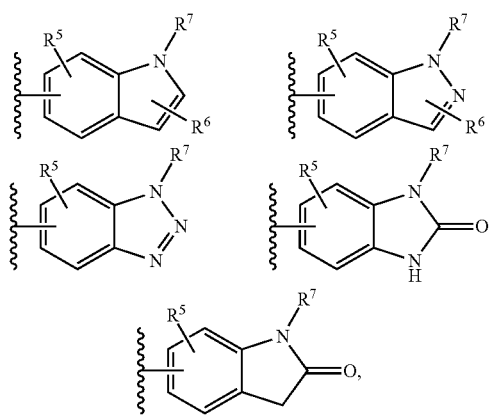

wherein each of $R^5$, $R^6$, and $R^7$, independently, is H, halo, nitro, cyano, aryl, heteroaryl, alkyl, alkenyl, alkynyl, cycloalkyl, heterocycloalkyl, cycloalkenyl, heterocycloalkenyl, —$OR^a$, —$C(O)R^a$, —$C(O)NR^aR^b$, —$NR^aC(O)R^b$, —$NR^aR^b$, —$S(O)_2R^a$, —$S(O)_2NR^aR^b$, —$NR^aS(O)_2R^b$, —N=$CR^aR^b$, or —$NR^aC(O)NHR^b$, wherein each of $R^a$ and $R^b$, independently, is H, alkyl, alkenyl, alkynyl, aryl, aryloxy, alkoxy, hydroxy, heteroaryl, cycloalkyl heterocycloalkyl, cycloalkenyl, or heterocycloalkenyl, or $R^a$ and $R^b$, together with the nitrogen atom to which they are bonded, form heteroaryl, heterocycloalkyl, or heterocycloalkenyl;

one of R¹ and R² is —OH or —OR^a and the other of R¹ and R² is —H, OH, or —OR^a,
R³, and R⁴ are independently H or —OR^a, wherein R^a is alkyl,
wherein the compound is:
2-methoxy-4-(4-(phenylamino)quinazolin-6-yl)phenol;
6-(3-fluoro-4-methoxyphenyl)-N-phenylquinazolin-4-amine;
6-(3-methoxyphenyl)-N-phenylquinazolin-4-amine;
4-(4-(phenylamino)quinazolin-6-yl)phenol;
6-(4-aminophenyl)-N-phenylquinazolin-4-amine;
2-methoxy-4-(4-(phenylamino)quinazolin-6-yl)phenyl phenylcarbamate;
4-(4-(3-hydroxyphenylamino)quinazolin-6-yl)-2-methoxyphenol;
2-methoxy-4-(4-(phenylamino)quinazolin-6-yl)phenyl ethylcarbamate;
6-(4-methoxyphenyl)-N-phenylquinazolin-4-amine;
4-(4-(3,4-dimethoxyphenylamino)quinazolin-6-yl)-2-methoxyphenol;
4-(4-(3-chloro-4-fluorophenylamino)quinazolin-6-yl)-2-methoxyphenol;
4-(4-(4-fluorophenylamino)quinazolin-6-yl)-2-methoxyphenol;
4-(4-(4-chloro-2-fluorophenylamino)quinazolin-6-yl)-2-methoxyphenol;
4-(4-(2-fluoro-4-methylphenylamino)quinazolin-6-yl)-2-methoxyphenol;
2-methoxy-4-(4-(3-(trifluoromethyl)phenylamino)quinazolin-6-yl)phenol;
4-(4-(4-hydroxyphenylamino)quinazolin-6-yl)-2-methoxyphenol;
4-(4-(2,4-difluorophenylamino)quinazolin-6-yl)-2-methoxyphenol;
4-(4-(4-chloro-2-hydroxyphenylamino)quinazolin-6-yl)-2-methoxyphenol;
2-methoxy-4-(4-(3-methoxyphenylamino)quinazolin-6-yl)phenol;
4-(4-(2-hydroxyphenylamino)quinazolin-6-yl)-2-methoxyphenol;
N-(4-(4-(phenylamino)quinazolin-6-yl)phenyl)ethanesulfonamide;
4-(4-(3-hydroxy-4-methoxyphenylamino)quinazolin-6-yl)-2-methoxyphenol;
3-(6-(4-hydroxy-3-methoxyphenyl)quinazolin-4-ylamino)benzene sulfonamide;
4-(4-(3-hydroxy-4-methylphenylamino)quinazolin-6-yl)-2-methoxyphenol;
2-methoxy-4-(7-methoxy-4-(phenylamino)quinazolin-6-yl)phenol;
4-(4-(3-hydroxyphenylamino)-7-methoxyquinazolin-6-yl)-2-methoxyphenol;
3-(6-(4-hydroxy-3-methoxyphenyl)quinazolin-4-ylamino)benzoic acid;
2-(6-(4-hydroxy-3-methoxyphenyl)quinazolin-4-ylamino)benzamide;
3-hydroxy-4-(6-(4-hydroxy-3-methoxyphenyl)quinazolin-4-ylamino)benzoic acid;
3-(6-(4-hydroxy-3-methoxyphenyl)quinazolin-4-ylamino)benzamide;
2-methoxy-4-(4-(3-nitrophenylamino)quinazolin-6-yl)phenol;
4-(4-(3-aminophenylamino)quinazolin-6-yl)-2-methoxyphenol;
4-(4-(benzo[d][1,3]dioxol-5-ylamino)quinazolin-6-yl)-2-methoxyphenol;
4-(4-(1H-indazol-6-ylamino)quinazolin-6-yl)-2-methoxyphenol;
4-(4-(1H-indol-6-ylamino)quinazolin-6-yl)-2-methoxyphenol;
4-(4-(3-hydroxy-4-methylphenylamino)-7-methoxyquinazolin-6-yl)-2-methoxyphenol;
4-(4-(3-hydroxy-4-methoxyphenylamino)-7-methoxyquinazolin-6-yl)-2-methoxyphenol;
4-(4-(2-chloro-5-hydroxyphenylamino)-7-methoxyquinazolin-6-yl)-2-methoxyphenol;
N-(3-(6-(4-hydroxy-3-methoxyphenyl)quinazolin-4-ylamino)phenyl)acetamide;
2,2,2-trifluoro-N-(3-(6-(4-hydroxy-3-methoxyphenyl)quinazolin-4-ylamino)phenyl)acetamide;
4-(6-(4-hydroxy-3-methoxyphenyl)quinazolin-4-ylamino)benzenesulfonamide;
4-(6-(4-hydroxy-3-methoxyphenyl)quinazolin-4-ylamino)benzamide;
2-(6-(4-hydroxy-3-methoxyphenyl)quinazolin-4-ylamino)-4-methoxybenzoic acid;
3-(6-(4-hydroxyphenyl)-7-methoxyquinazolin-4-ylamino)phenol;
2-(6-(4-hydroxy-3-methoxyphenyl)quinazolin-4-ylamino)benzoic acid;
4-(4-(1H-indazol-4-ylamino)quinazolin-6-yl)-2-methoxyphenol;
4-(4-(3-fluorophenylamino)quinazolin-6-yl)-2-methoxyphenol;
3-(6-(4-hydroxy-3-methoxyphenyl)quinazolin-4-ylamino)-2-methylphenol;
4-(4-(1H-benzo[d]imidazol-6-ylamino)quinazolin-6-yl)-2-methoxyphenol;
4-(4-(5-hydroxy-2-methoxyphenylamino)quinazolin-6-yl)-2-methoxyphenol;
N-(3-(6-(4-hydroxy-3-methoxyphenyl)quinazolin-4-ylamino)phenyl)methanesulfonamide;
4-(6-(4-hydroxy-3-methoxyphenyl)quinazolin-4-ylamino)benzoic acid;
4-(4-(2-fluoro-5-hydroxyphenylamino)quinazolin-6-yl)-2-methoxyphenol;
4-(4-(2-chloro-5-hydroxyphenylamino)quinazolin-6-yl)-2-methoxyphenol;
2-chloro-3-(6-(4-hydroxy-3-methoxyphenyl)quinazolin-4-ylamino)phenol;
2,4-dichloro-5-(6-(4-hydroxy-3-methoxyphenyl)quinazolin-4-ylamino)phenol;
3-(6-(4-hydroxyphenyl)quinazolin-4-ylamino)phenol;
3-(6-(3-hydroxyphenyl)quinazolin-4-ylamino)phenol;
3-(6-(4-methoxyphenyl)quinazolin-4-ylamino)phenol;
1,1,1-trifluoro-N-(3-(6-(4-hydroxy-3-methoxyphenyl)quinazolin-4-ylamino)phenyl)methanesulfonamide;
4-(4-(1H-benzo[d][1,2,3]triazol-5-ylamino)quinazolin-6-yl)-2-methoxyphenol;
3-(6-(3-methoxyphenyl)quinazolin-4-ylamino)phenol;
6-(2-fluoro-3-methoxyphenyl)-N-(1H-indazol-4-yl)quinazolin-4-amine;
6-(3-fluoro-4-methoxyphenyl)-N-(1H-indazol-4-yl)quinazolin-4-amine;
6-(3-chloro-4-methoxyphenyl)-N-(1H-indazol-4-yl)quinazolin-4-amine;
N-(1H-indazol-4-yl)-6-(4-methoxy-2-methylphenyl)quinazolin-4-amine;
N-(1H-indazol-4-yl)-6-(4-methoxy-3-methylphenyl)quinazolin-4-amine;
4-(4-(1H-benzo[d][1,2,3]triazol-4-ylamino)quinazolin-6-yl)-2-methoxyphenol;

4-(4-(1H-indol-4-ylamino)quinazolin-6-yl)-2-methoxyphenol;
6-(4-fluoro-3-methoxyphenyl)-N-(1H-indazol-4-yl)quinazolin-4-amine;
6-(3,4-dimethoxyphenyl)-N-(1H-indazol-4-yl)quinazolin-4-amine;
6-(4-ethoxyphenyl)-N-(1H-indazol-4-yl)quinazolin-4-amine;
5-(4-(1H-indazol-4-ylamino)quinazolin-6-yl)-2-methoxybenzaldehyde;
2-methoxy-4-(4-(1-methyl-1H-indazol-4-ylamino)quinazolin-6-yl)phenol;
4-(4-(3-hydroxyphenylamino)quinolin-6-yl)-2-methoxyphenol;
4-(4-(2-fluoro-5-hydroxyphenylamino)quinolin-6-yl)-2-methoxyphenol;
4-(4-(1H-indazol-4-ylamino)quinolin-6-yl)-2-methoxyphenol;
6-(2,3-dimethoxyphenyl)-N-(1H-indazol-4-yl)quinazolin-4-amine;
6-(2-fluoro-3-methoxyphenyl)-N-(1H-indazol-4-yl)quinolin-4-amine;
6-(3-fluoro-4-methoxyphenyl)-N-(1H-indazol-4-yl)quinolin-4-amine;
6-(3,4-dimethoxyphenyl)-N-(1H-indazol-4-yl)quinolin-4-amine;
6-(3-chloro-4-methoxyphenyl)-N-(1H-indazol-4-yl)quinolin-4-amine;
5-(4-(1H-indazol-4-ylamino)quinolin-6-yl)-2-methoxybenzaldehyde;
4-(4-(3-(difluoromethoxy)phenylamino)quinazolin-6-yl)-2-methoxyphenol;
4-(4-(2-fluorophenylamino)quinazolin-6-yl)-2-methoxyphenol;
N-(1H-indazol-4-yl)-6-(4-(methylsulfonyl)phenyl)quinolin-4-amine;
N-(1H-indazol-4-yl)-6-(3-methoxyphenyl)quinolin-4-amine;
4-(4-(1H-indazol-4-ylamino)quinolin-6-yl)phenol;
4-(4-(3-chloro-1H-indazol-4-ylamino)quinazolin-6-yl)-2-methoxyphenol;
4-(6-(4-hydroxy-3-methoxyphenyl)quinazolin-4-ylamino)-1H-benzo[d]imidazol-2(3H)-one;
N-(4-fluoro-3-(6-(4-hydroxy-3-methoxyphenyl)quinolin-4-ylamino)phenyl)methanesulfonamide;
N-(4-fluoro-3-(6-(4-hydroxy-3-methoxyphenyl)quinazolin-4-ylamino)phenyl)methanesulfonamide;
N-(2-fluoro-5-(6-(4-hydroxy-3-methoxyphenyl)quinazolin-4-ylamino)phenyl)methanesulfonamide;
4-(4-(1H-indazol-4-ylamino)quinazolin-6-yl)phenol;
3-(6-phenylquinazolin-4-ylamino)phenol;
4-(4-(2,6-difluorophenylamino)quinazolin-6-yl)-2-methoxyphenol;
4-(1H-indazol-4-ylamino)-6-(4-hydroxy-3-methoxyphenyl)quinoline-3-carbonitrile;
4-(4-(5-fluoro-1H-indazol-4-ylamino)quinazolin-6-yl)-2-methoxyphenol;
N-(4-chloro-3-(6-(4-hydroxy-3-methoxyphenyl)quinazolin-4-ylamino)phenyl)methanesulfonamide;
N-(2-chloro-5-(6-(4-hydroxy-3-methoxyphenyl)quinazolin-4-ylamino)phenyl)methanesulfonamide;
N-(2-chloro-5-(6-(4-hydroxy-3-methoxyphenyl)quinolin-4-ylamino)phenyl)methanesulfonamide;
3-(4-(1H-indazol-4-ylamino)quinazolin-6-yl)phenol;
N-(1H-indazol-4-yl)-6-(3-methoxyphenyl)quinazolin-4-amine;
N-(2-fluoro-5-(6-(4-hydroxy-3-methoxyphenyl)quinolin-4-ylamino)phenyl)methanesulfonamide;
N-(1H-indazol-4-yl)-6-(3-methoxyphenyl)quinolin-4-amine;
N-(1H-indazol-4-yl)-6-(4-methoxyphenyl)quinazolin-4-amine;
3-(4-(1H-indazol-4-ylamino)quinolin-6-yl)phenol;
4-(4-(5-fluoro-1H-indazol-4-ylamino)quinazolin-6-yl)-2-methoxyphenol;
N-(2,4-difluoro-5-(6-(4-hydroxy-3-methoxyphenyl)quinazolin-4-ylamino)phenyl)methanesulfonamide;
N-(3-ethynylphenyl)-6-(4-methoxyphenyl)quinazolin-4-amine;
3-(6-(4-methoxyphenyl)quinazolin-4-yloxy)phenol;
4-(4-(5-hydroxy-2-methylphenylamino)quinazolin-6-yl)-2-methoxyphenol;
2-methoxy-4-(4-(5-methyl-1H-indazol-4-ylamino)quinazolin-6-yl)phenol;
4-fluoro-5-(6-(4-hydroxy-3-methoxyphenyl)quinazolin-4-ylamino)-2-methylphenol;
4-(4-(4-chloro-3-hydroxyphenylamino)quinazolin-6-yl)-2-methoxyphenol;
2,4-difluoro-5-(6-(4-hydroxy-3-methoxyphenyl)quinazolin-4-ylamino)phenol;
2-chloro-4-fluoro-5-(6-(4-hydroxy-3-methoxyphenyl)quinazolin-4-ylamino)phenol;
5-(6-(4-chlorophenyl)quinazolin-4-ylamino)-2,4-difluorophenol;
4-(4-(4-fluoro-3-hydroxyphenylamino)quinazolin-6-yl)-2-methoxyphenol;
2,6-difluoro-3-(6-(4-hydroxy-3-methoxyphenyl)quinazolin-4-ylamino)phenol;
3-(6-(1H-indazol-5-yl)quinazolin-4-ylamino)-2,6-difluorophenol; or
3-(6-(4-chlorophenyl)quinazolin-4-ylamino)-2,6-difluorophenol.

* * * * *